United States Patent
Nishimura

(10) Patent No.: US 11,013,985 B2
(45) Date of Patent: May 25, 2021

(54) INFORMATION PROCESSING DEVICE AND INFORMATION PROCESSING METHOD

(71) Applicant: SONY CORPORATION, Tokyo (JP)

(72) Inventor: Kiminobu Nishimura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/475,861

(22) PCT Filed: Dec. 15, 2017

(86) PCT No.: PCT/JP2017/045101
§ 371 (c)(1),
(2) Date: Jul. 3, 2019

(87) PCT Pub. No.: WO2018/163558
PCT Pub. Date: Sep. 13, 2018

(65) Prior Publication Data
US 2019/0381396 A1  Dec. 19, 2019

(30) Foreign Application Priority Data
Mar. 8, 2017  (JP) .............................. JP2017-044231

(51) Int. Cl.
*A63F 13/212*  (2014.01)
*A63F 13/5375*  (2014.01)
(Continued)

(52) U.S. Cl.
CPC ........ *A63F 13/212* (2014.09); *A63F 13/5375* (2014.09); *A63F 13/58* (2014.09);
(Continued)

(58) Field of Classification Search
None
See application file for complete search history.

(56) References Cited

U.S. PATENT DOCUMENTS

| 8,647,204 B2 * | 2/2014 | Kando | A63F 13/10 463/37 |
| 10,401,799 B2 * | 9/2019 | Kusuda | G04G 13/021 |

(Continued)

FOREIGN PATENT DOCUMENTS

| AU | 2010293013 A1 | 5/2012 |
| EP | 2477538 A2 | 7/2012 |

(Continued)

OTHER PUBLICATIONS

International Search Report and Written Opinion of PCT Application No. PCT/JP2017/045101, dated Mar. 13, 2018, 14 pages of ISWRO.

*Primary Examiner* — Ronald Laneau
(74) *Attorney, Agent, or Firm* — Chip Law Group

(57) ABSTRACT

There is provided an information processing device including a control unit that determines, on the basis of an item to be improved which item is set on the basis of a health index calculated from collected sensor information, an improving process to improve the item to be improved and a reward that is related to an amusement and that is served in a case where the item to be improved is improved. The control unit further presents contents of the improving process and the reward to a user, in which the control unit determines whether or not the item to be improved is improved on the basis of a variation in the health index, and makes a controlled object perform an operation corresponding to the reward on the basis of the determination that the item to be improved is improved.

20 Claims, 21 Drawing Sheets

(51) Int. Cl.
    *A63F 13/58*    (2014.01)
    *A63F 13/69*    (2014.01)
(52) U.S. Cl.
    CPC ........ *A63F 13/69* (2014.09); *A63F 2250/142* (2013.01); *A63F 2300/1012* (2013.01)

(56) References Cited

U.S. PATENT DOCUMENTS

| | | |
|---|---|---|
| 2011/0230732 A1 | 9/2011 | Edman et al. |
| 2012/0309542 A1* | 12/2012 | Nogami ................. A63F 13/31 463/42 |
| 2014/0017644 A1 | 1/2014 | Edman et al. |
| 2014/0058703 A1* | 2/2014 | Kimishima ............. G04F 10/00 702/177 |
| 2016/0328524 A1 | 11/2016 | Kawai et al. |
| 2017/0136348 A1* | 5/2017 | Hattori ................... A61B 5/742 |
| 2018/0283932 A1* | 10/2018 | Yukino ................ A61B 5/0537 |

FOREIGN PATENT DOCUMENTS

| | | |
|---|---|---|
| EP | 3096239 A1 | 11/2016 |
| JP | 2013-509205 A | 3/2013 |
| JP | 2014-237058 A | 12/2014 |
| WO | 2011/031335 A2 | 3/2011 |
| WO | 2015/107748 A1 | 7/2015 |
| WO | 2016/021235 A1 | 2/2016 |

\* cited by examiner

FIG. 16
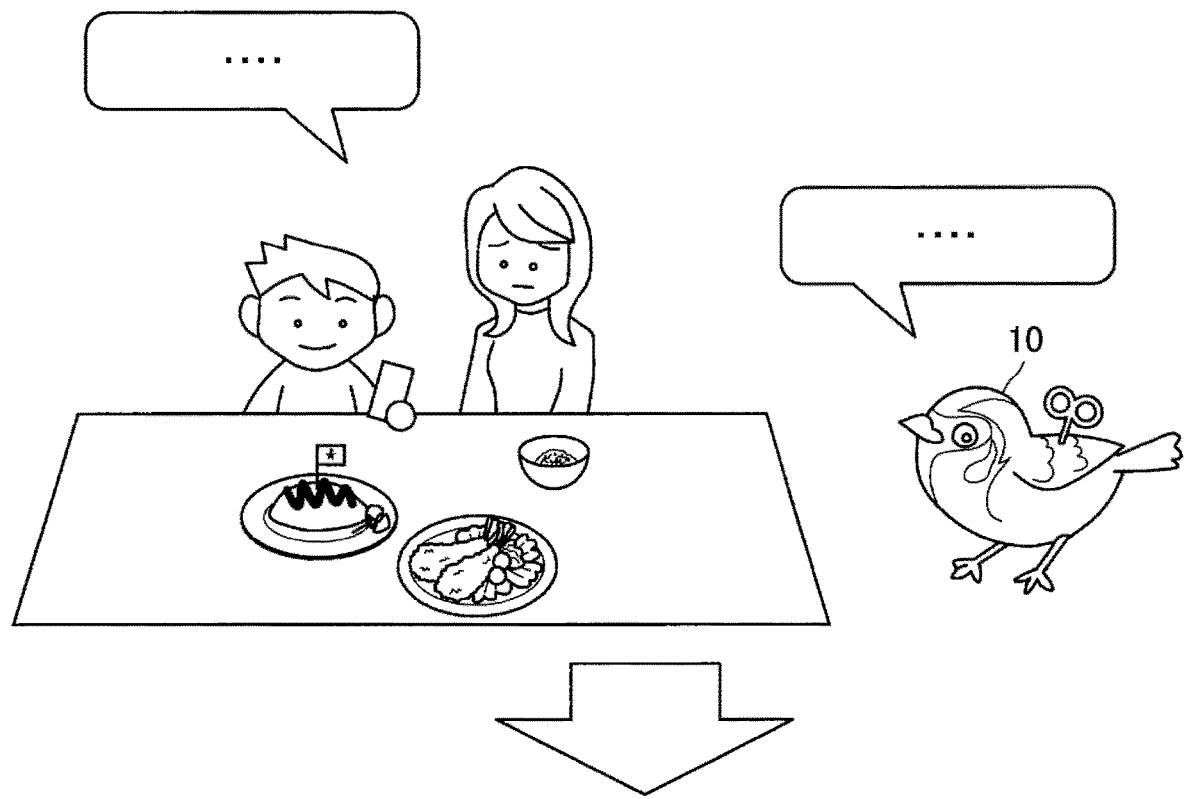
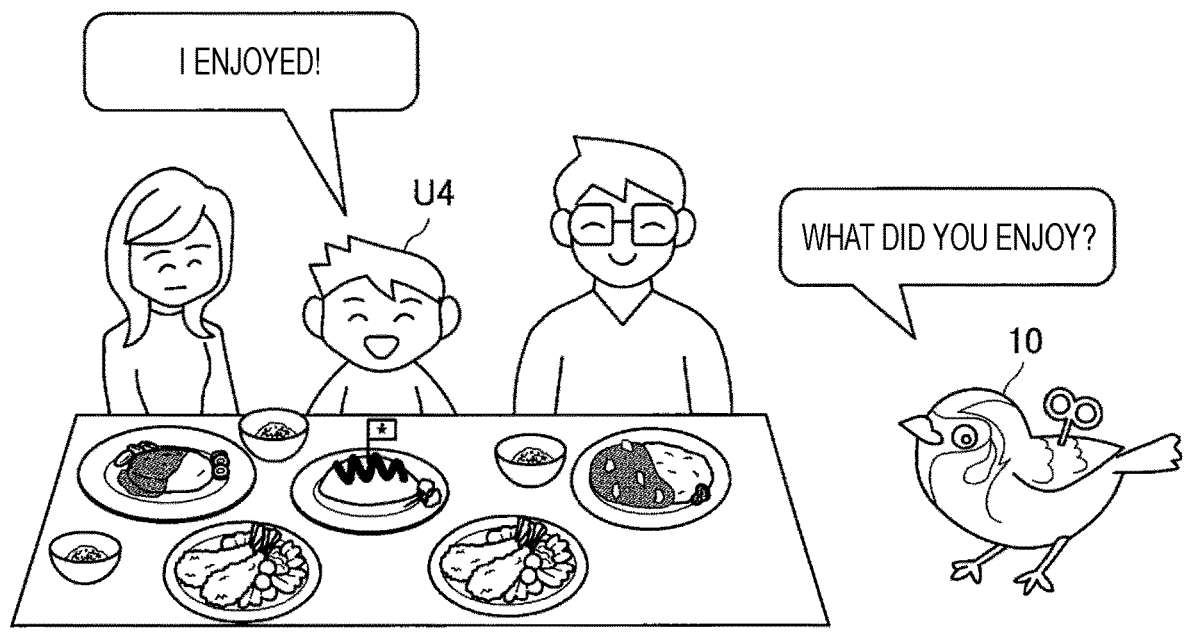

FIG. 20
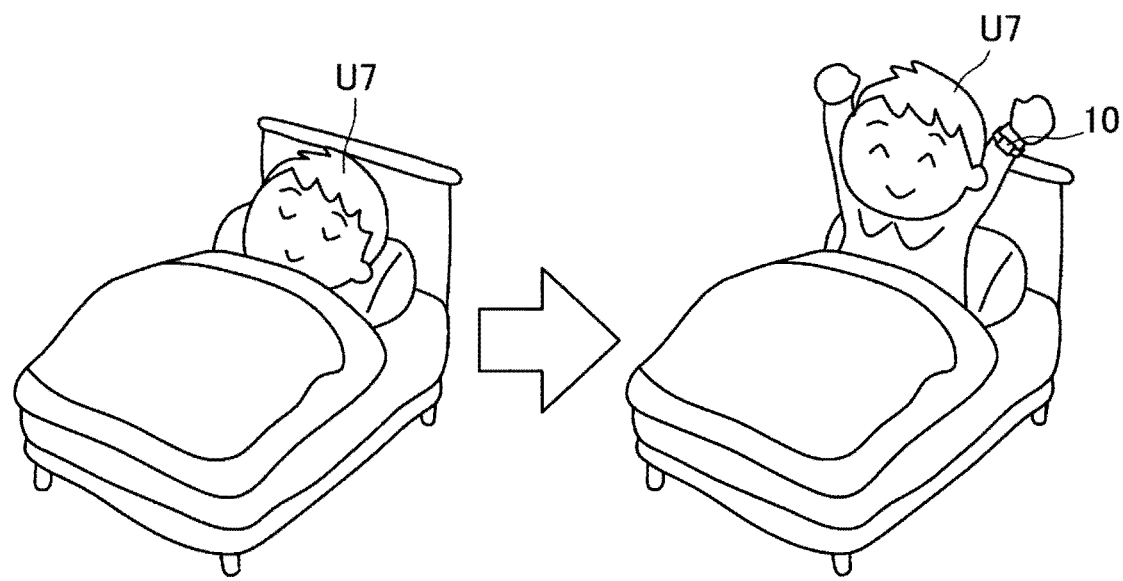
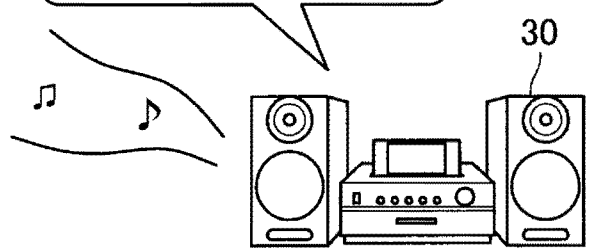
SINCE GETTING UP WITHOUT FALLING BACK TO SLEEP, YOU CAN HEAR NEW SONG

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2017/045101 filed on Dec. 15, 2017, which claims priority benefit of Japanese Patent Application No. JP 2017-044231 filed in the Japan Patent Office on Mar. 8, 2017. Each of the above-referenced applications is hereby incorporated herein by reference in its entirety.

TECHNICAL FIELD

The present disclosure relates to an information processing device, an information processing method, and a program.

BACKGROUND ART

Recently, a device that performs various kinds of analysis on the basis of collected sensor information is widespread. Furthermore, a technology of controlling an operation of a device on the basis of a result of analysis using sensor information is also developed. For example, a technology of analyzing a health condition on the basis of collected biological information or the like of a user, reflecting the health condition on expression or motion of a displayed character, and performing presentation thereof to the user is disclosed in Patent Document 1.

CITATION LIST

Patent Document

Patent Document 1: Japanese Patent Application Laid-Open No. 2014-237058

SUMMARY OF THE INVENTION

Problems to be Solved by the Invention

However, a technology described in Patent Document 1 puts emphasis on making a user perceive a health condition. Thus, it is required for a user himself/herself to select a means to improve the health condition, or the like each time after checking the health condition. Thus, it is hard to say that the technology described in Patent Document 1 has an enough effect for encouraging an action change of a user.

Thus, a new and improved information processing device, information processing method, and program that are capable of more effectively encouraging a user to make an action change related to improvement in a health condition are proposed in the present disclosure.

Solutions to Problems

According to the present disclosure, there is provided an information processing device including: a control unit configured to determine, on the basis of an item to be improved which item is set on the basis of a health index calculated from collected sensor information, an improving means to improve the item to be improved and a reward that is related to an amusement and that is served in a case where the item to be improved is improved, and configured to present contents of the improving means and the reward to a user, in which the control unit determines whether or not the item to be improved is improved on the basis of a variation in the health index, and makes a controlled object perform an operation corresponding to the reward on the basis of the determination that the item to be improved is improved.

Furthermore, according to the present disclosure, there is provided an information processing method including: calculating, by a processor, a health index on the basis of collected sensor information, setting an item to be improved on the basis of the health index; determining an improving means to improve the item to be improved and a reward that is related to an amusement and that is served in a case where the item to be improved is improved; presenting contents of the improving means and the reward to a user; determining whether or not the item to be improved is improved on the basis of a variation in the health index; and performing an operation corresponding to the reward on the basis of the determination that the item to be improved is improved.

Furthermore, according to the present disclosure, there is provided a program for causing a computer to function as an information processing device including a control unit configured to determine, on the basis of an item to be improved which item is set on the basis of a health index calculated from collected sensor information, an improving means to improve the item to be improved and a reward that is related to an amusement and that is served in a case where the item to be improved is improved, and configured to present contents of the improving means and the reward to a user, in which the control unit determines whether or not the item to be improved is improved on the basis of a variation in the health index, and makes a controlled object perform an operation corresponding to the reward on the basis of the determination that the item to be improved is improved.

Effects of the Invention

As described above, it becomes possible to more effectively encourage a user to make an action change related to improvement in a health condition according to the present disclosure.

Note that the above effect is not necessarily a limitation. In addition to the above effect or instead of the above effect, any of effects indicated in the present description, or a different effect that may be grasped from the present description may be acquired.

BRIEF DESCRIPTION OF DRAWINGS

FIG. 16 is a view for describing an outline of a seventh example according to the embodiment.

FIG. 20 is a view for describing an outline of an eleventh example according to the embodiment.

MODE FOR CARRYING OUT THE INVENTION

In the following, a preferred embodiment of the present disclosure will be described in detail with reference to the attached drawings. Note that the same sign is assigned to configuration elements having substantially the same functional configuration and an overlapped description thereof is omitted in the present description and drawings.

Note that the description will be made in the following order.
1. Embodiment
1.1. Outline of one embodiment
1.2. System configuration example
1.3. Functional configuration example of information processing terminal 10
1.4. Functional configuration example of information processing device 20
1.5. Flow of operation of information processing device 20
1.6. First example
1.7. Second example
1.8. Third example
1.9. Fourth example
1.10. Fifth example
1.11. Sixth example
1.12. Seventh example
1.13. Eighth example
1.14. Ninth example
1.15. Tenth example
1.16. Eleventh example
1.17. Twelfth example
2. Hardware configuration example
3. Conclusion 1. Embodiment 1.1. Outline of One Embodiment First, an outline of one embodiment of the present disclosure will be described. As described above, recently, a device that analyzes a health condition of a user on the basis of collected sensor information and presents the health condition to the user is developed. However, in many cases, a function of such a device described above is limited only to presentation of a health condition to a user. Thus, it is assumed that there is a condition in which the user cannot grasp how to act to improve the health condition.

Furthermore, for example, even in a case where a means to improve a health condition is presented, a mental/physical burden of an action for health improvement is often heavy for the user and there is a case where it is difficult to continue such an action described above. On the one hand, it is assumed that the user is willing to execute and continue an action corresponding to a taste even in a case where there is some burden.

The present technical idea is inspired by a focus on the above point and enables effective induction of an action of a user by presenting an improving means that is more easily executed or continued. Thus, an information processing device, an information processing method, and a program according to the present embodiment present a reward, which is served when improvement is achieved, to a user along with an improving means to improve a health condition. Here, the above reward may correspond to a taste, specifically, a taste related to an amusement of a user. According to the above characteristic, it becomes possible to encourage a voluntary action of a user by using a desire of the user for acquiring reward, and a high health improvement effect can be expected.

1.2. System Configuration Example

Figure 1:
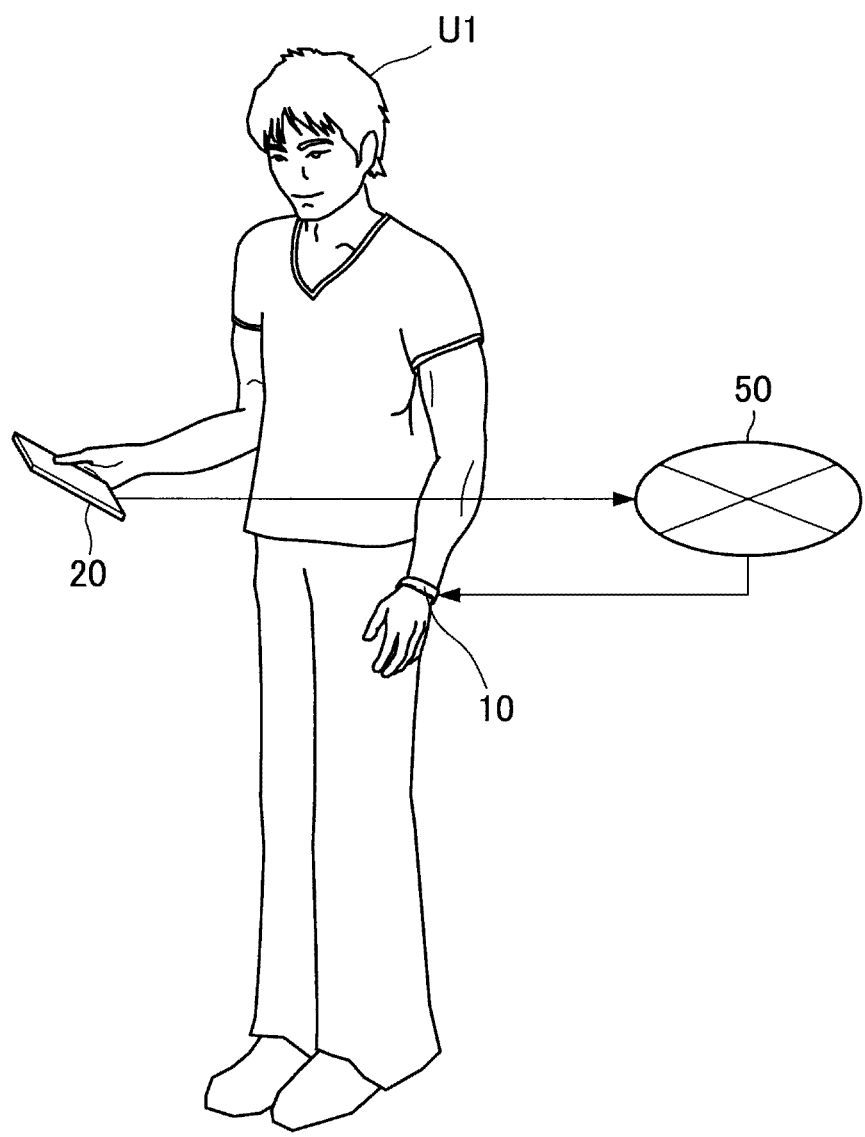
FIG. 1 is a view illustrating a system configuration example of an information processing system according to one embodiment of the present disclosure.

Next, a system configuration example of an information processing system according to the present embodiment will be described. FIG. 1 is a view illustrating a system configuration example of the information processing system according to the present embodiment. As illustrated in FIG. 1, the information processing system according to the present embodiment may include an information processing terminal 10 and an information processing device 20. Furthermore, the information processing terminal 10 and the information processing device 20 are connected in such a manner that mutual communication can be performed through a network 50.

(Information Processing Terminal 10)

The information processing terminal 10 according to the present embodiment is an information processing device that collects various kinds of sensor information related to a user. The sensor information collected by the information processing terminal 10 can be used for calculation of a health index or action estimation by the information processing device 20. The information processing terminal 10 according to the present embodiment may be, for example, a cell-phone, a smartphone, a tablet, or various wearable devices held by a user. In FIG. 1, one example of a case where the information processing terminal 10 according to the present embodiment is a wristband-type wearable device held by a user is illustrated.

(Information Processing Device 20)

The information processing device 20 according to the present embodiment has a function of calculating a health index of a user on the basis of sensor information collected by the information processing terminal 10, and determining an item to be improved which item requires improvement. For example, an example of the item to be improved includes an amount of sleep, an amount of activity, or the like. Furthermore, the information processing device 20 according to the present embodiment has a function of determining, on the basis of an item to be improved in the above manner, an improving means to improve the item to be improved and a reward that is related to an amusement and that is served in a case where the item to be improved is achieved. Moreover, the information processing device 20 according to the present embodiment has a function of controlling presentation of the above improving means and reward to the user.

In FIG. 1, an example of a case where the information processing device 20 according to the present embodiment is a smartphone held by a user is illustrated. In this case, the information processing device 20 may display contents of the improving means and the reward on a display unit of the smartphone.

Furthermore, the information processing device 20 according to the present embodiment has a function of determining whether or not an item to be improved is improved on the basis of a variation in a health index successively calculated. Moreover, the information processing device 20 has a function of controlling provision of reward to a user. Specifically, the information processing device 20 may perform control of providing reward to a user in a case of estimating that an item to be improved is improved. For example, in a case of the one example illustrated in FIG. 1, the information processing device 20 can make an operation unit of the smartphone perform an operation corresponding to reward.

Note that although one example in a case where the information processing device 20 is a smartphone is illustrated in FIG. 1, an information processing device 20 according to the present embodiment is not limited to such an example. For example, an information processing device 20 according to the present embodiment may be a server or the like arranged in a cloud. In this case, the information processing device 20 can control a smartphone or the like, which is held by the user, to perform presentation of contents of an improving means and reward, provision of the reward, or the like.

Furthermore, the information processing device 20 according to the present embodiment may make different controlled objects respectively perform presentation of contents of an improving means and reward, and provision of the reward. For example, the information processing device 20 can make a television devise present contents of an improving means and reward, and make a smartphone provide the reward. In such a manner, a form of the information processing device 20 or a controlled object of the information processing device 20 according to the present embodiment may be changed flexibly according to a specification or operation.

1.3. Functional Configuration Example of Information Processing Terminal 10

Figure 2:
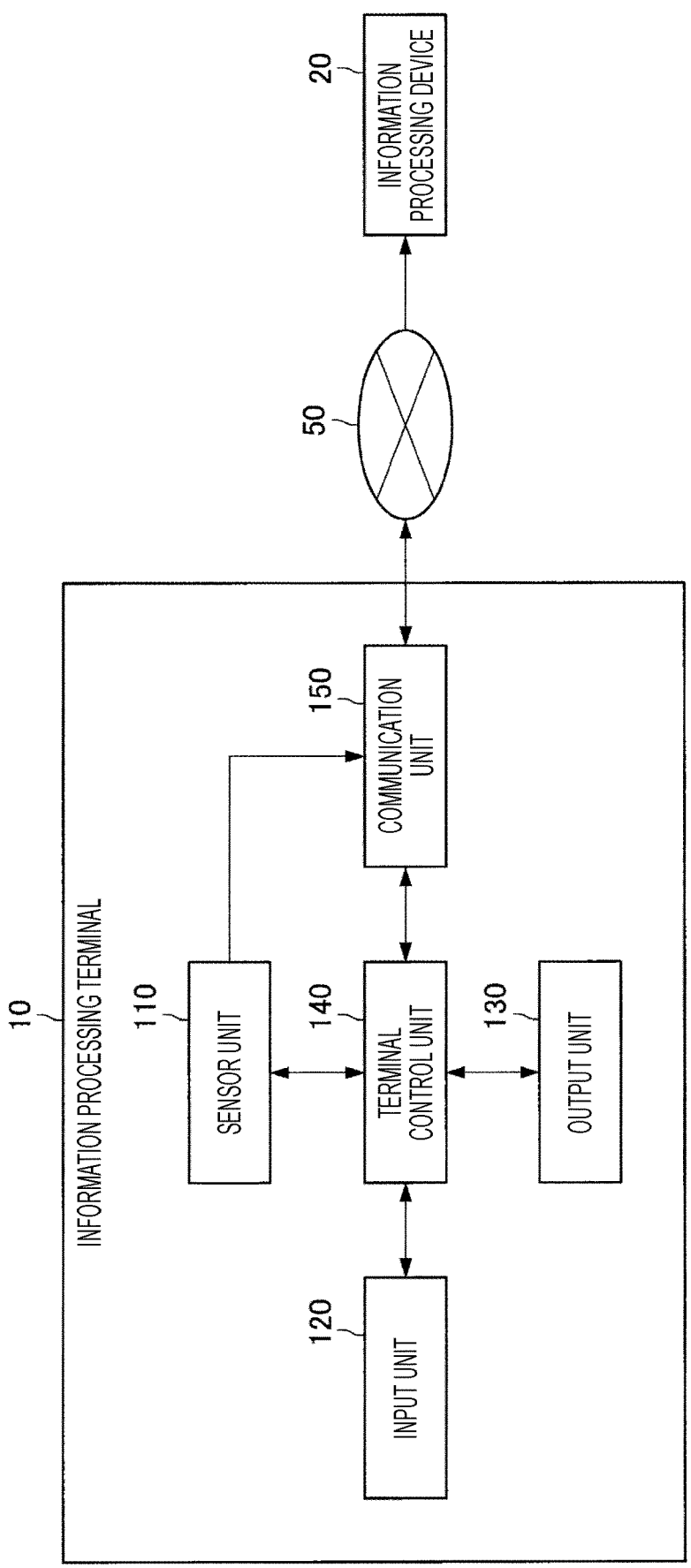
FIG. 2 is an example of a functional block diagram of an information processing terminal according to the embodiment.

Next, a functional configuration example of the information processing terminal 10 according to the present embodiment will be described. FIG. 2 is one example of a functional block diagram of the information processing terminal 10 according to the present embodiment. As illustrated in FIG. 2, the information processing terminal 10 according to the present embodiment may include a sensor unit 110, an input unit 120, an output unit 130, a terminal control unit 140, and a communication unit 150.

(Sensor Unit 110)

The sensor unit 110 has a function of collecting various kinds of sensor information related to a user. As described above, the sensor information collected by the sensor unit 110 is used for calculation of a health index by the information processing device 20. Thus, the sensor information collected by the sensor unit 110 may include biological information of the user. Here, the above biological information includes, for example, information such as a pulse wave, perspiration, blood pressure, myoelectric potential, a cardiac electrogram, ocular potential, a brain wave, a pupillary opening rate, or body temperature. Thus, the sensor unit 110 includes a sensor to collect such biological information described above.

Furthermore, the sensor unit 110 may collect sensor information used for action estimation by the information processing device 20. Thus, the sensor unit 110 includes, for example, an acceleration sensor, a gyroscope sensor, an atmospheric pressure sensor, a temperature sensor, a humidity sensor, a myoelectric sensor, a microphone, a vibration sensor, a pressure sensor, an imaging sensor, a GPS sensor, or the like.

(Input Unit 120)

The input unit 120 has a function of receiving input operation by a user. Thus, the input unit 120 according to the present embodiment may include various devices or sensors to detect the input operation by the user. For example, the input unit 120 includes a touch panel, a button, a keyboard, a switch, or the like. Furthermore, the input unit 120 may include a microphone to collect a sound of the user.

(Output Unit 130)

The output unit 130 has a function of presenting visual information and sound information to a user. Thus, the output unit 130 according to the present embodiment includes, for example, a touch panel, a liquid crystal display (LCD) device, an organic light emitting diode (OLED) device, or the like. Furthermore, the output unit 130 according to the present embodiment may include a speaker or an amplifier to output sound. Note that the output unit 130 according to the present embodiment may be a controlled object of the information processing device 20. Thus, the output unit 130 according to the present embodiment may output contents of an improving means and reward on the basis of control by the information processing device 20. Furthermore, the output unit 130 may provide reward to a user on the basis of the control by the information processing device 20.

(Terminal Control Unit 140)

The terminal control unit 140 has a function of controlling an operation of each configuration included in the information processing terminal 10. Furthermore, for example, the terminal control unit 140 controls an operating system (OS) or various applications installed in the information processing terminal 10.

(Communication Unit 150)

The communication unit 150 has a function of performing information communication with the information processing device 20 through the network 50. Specifically, the communication unit 150 transmits sensor information collected by the sensor unit 110 to the information processing device 20.

Furthermore, the communication unit 150 may receive a control signal related to presentation of contents of an improving means and reward, or to provision of the reward.

In the above, a functional configuration example of the information processing terminal 10 according to the present embodiment has been described. Note that the above functional configuration described with reference to FIG. 2 is just an example, and a functional configuration of the information processing terminal 10 according to the present embodiment is not limited to such an example. For example, the information processing terminal 10 according to the present embodiment does not necessarily include all of the above-described configurations. Furthermore, the information processing terminal 10 may further include a configuration other than what is illustrated in FIG. 2. A functional configuration of the information processing terminal 10 according to the present embodiment may be modified flexibly according to a specification or operation.

1.4. Functional Configuration Example of Information Processing Device 20

Figure 3:
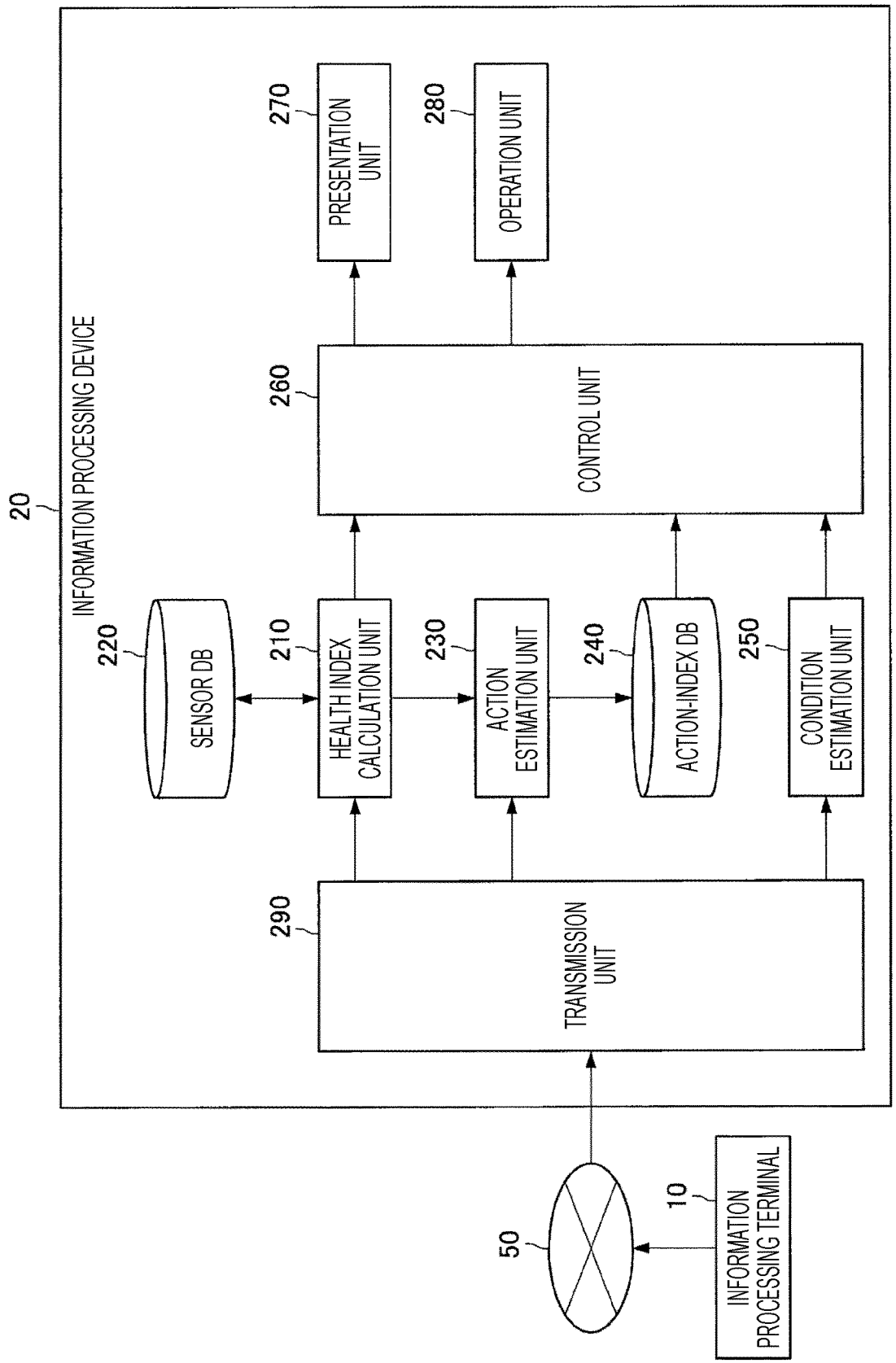
FIG. 3 is an example of a functional block diagram of an information processing device according to the embodiment.

Next, a functional configuration example of the information processing device 20 according to the present embodiment will be described. FIG. 3 is one example of a functional block diagram of the information processing device 20 according to the present embodiment. As illustrated in FIG. 3, the information processing device 20 according to the present embodiment may include a health index calculation unit 210, a sensor DB 220, an action estimation unit 230, an action-index DB 240, a condition estimation unit 250, a control unit 260, a presentation unit 270, an operation unit 280, and a communication unit 290.

(Health Index Calculation Unit 210)

The health index calculation unit 210 has a function of calculating a health index on the basis of sensor information collected by the information processing terminal 10. Furthermore, the health index calculation unit 210 according to the present embodiment has a function of setting an item to be improved, the item requiring improvement, on the basis of the calculated health index. Here, the health index according to the present embodiment may include a plurality of different items as illustrated in Chart 1 in the following.

CHART 1

| Health Index Item | Sensor Information | Information Processing Terminal |
|---|---|---|
| Amount of Sleep | Acceleration, Pulse Wave | Wearable Device |
| Amount of Activity | Acceleration, GPS | Smartphone |
| Sympathetic Activity Level | Cardiac Electrogram, Pulse Wave, Perspiration | Wearable Device |
| Parasympathetic Activity Level | Cardiac Electrogram, Pulse Wave, Perspiration | Wearable Device |
| Depression | Brain Wave, Pulse Wave | Head-Mounted Display |
| Lack of Communication | Microphone | Wearable Device |
| Unbalanced Diet | Imaging Sensor | Diet Contents Recognition Device |

In Chart 1 described above, one example of an item of a health index, sensor information used for calculation of the item, and a type of an information processing terminal 10 that collects the sensor information which example is according to the present embodiment is illustrated. For example, as illustrated in Chart 1, the health index calculation unit 210 according to the present embodiment may calculate an amount of sleep on the basis of acceleration information or pulse wave information collected by a wearable device-type information processing terminal 10. More specifically, the health index calculation unit 210 may recognize rolling over from acceleration and determine quality of sleep on the basis of the number of times of the rolling over. Furthermore, the health index calculation unit 210 can calculate a heart rate from the pulse wave information, separate a temporal variation of the heart rate into a low frequency (LF) component and a high frequency (HF) component by frequency conversion, and use a ratio between the two (LF/HF) as an index of activity of an autonomic nerve.

In such a manner, the health index calculation unit 210 according to the present embodiment can calculate a health index related to a plurality of items by performing a noise removal or characteristic extraction corresponding to the sensor information. Furthermore, the health index calculation unit 210 according to the present embodiment may set an item to be improved on the basis of a calculated value of each of the plurality of items. For example, the health index calculation unit 210 can set, as an item to be improved, an item with the largest difference from a determined standard among a plurality of items. Specifically, in a case where a calculated amount of sleep is eight hours, an amount of activity (energy consumption amount) is 200 kcal, and determined standards are six hours and 450 kcal respectively, the health index calculation unit 210 may set the amount of activity as an item to be improved on the basis of the amount of activity being lower than the standard. According to the above function included in the health index calculation unit 210 according to the present embodiment, it becomes possible to present a more important item to be improved to a user. Furthermore, for example, an effect of pointing out a health condition that the user is not aware of is expected.

Note that a health index according to the present embodiment does not necessarily include a plurality of items. Even in a case where a health index relates to a single item, the health index calculation unit 210 can compare the item with a standard value, and can set the item as an item to be improved in a case where a calculated value is lower than the standard value.

Furthermore, the health index calculation unit 210 according to the present embodiment may perform an operation using sensor information, which is collected at the same time, by using a machine learning technology such as a neural network. According to the above, it becomes possible to learn a conversion equation or the like of estimating a health index, which is acquired by utilization of single piece of sensor information, on the basis of a relationship between a plurality of biological signals, and it is possible to calculate a more accurate or general health index.

For example, the health index calculation unit 210 may perform supervised learning by using information related to perspiration and a pulse wave. Here, the health index calculation unit 210 can perform learning with a sympathetic activity level, which is calculated from the perspiration information and has high reliability, as a teacher and the pulse wave information as a student. According to the above learning, it is possible to acquire a conversion equation of estimating a sympathetic activity level on the basis of input pulse wave information, and it becomes possible to estimate the sympathetic activity level by using only the pulse wave information even in a case where sensor information related to perspiration cannot be acquired.

(Sensor DB 220)

The sensor DB 220 is a database that accumulates sensor information collected by the information processing terminal 10. The sensor DB 220 according to the present embodiment has a function of storing different kinds of sensor information, which is collected at the same time, along a time axis. In such a manner, since the sensor DB 220 stores a plurality of kinds of sensor information acquired at the same time, the health index calculation unit 210 can perform learning in the above-described manner.

(Action Estimation Unit 230)

The action estimation unit 230 has a function of estimating an action of a user on the basis of sensor information collected by the information processing terminal 10. For example, the action estimation unit 230 according to the present embodiment can estimate an action of the user which action corresponds to an improving means that is to improve an item to be improved and is determined by the control unit 260. Here, the improving means according to the present embodiment may include an action type and intensity of the action type. In other words, the action estimation unit 230 according to the present embodiment can estimate whether or not the user performs an action corresponding to the improving means or to which degree of intensity the action is performed.

Furthermore, the action estimation unit 230 according to the present embodiment has a function of associating the estimated action of the user and a health index calculated by the health index calculation unit 210, and making the action-index DB 240 perform storing thereof in time series. According to the above function included in the action estimation unit 230 according to the present embodiment, the control unit 260 can determine a more effective improving means or reward as described later.

(Action-Index DB 240)

The action-index DB 240 is a database that associates an estimated action of a user and a calculated health index and performs storing thereof in time series on the basis of control by the action estimation unit 230. For example, the action-index DB 240 stores a variation in a health index while the user performs an action A, a variation in a health index while the user performs an action B, or the like.

(Condition Estimation Unit 250)

The condition estimation unit 250 has a function of estimating a condition of a user. The condition of the user which condition is estimated by the condition estimation unit 250 may be used for determination of an improving means or reward by the control unit 260. Here, for example, the above condition of the user includes a schedule of the user. For example, the condition estimation unit 250 according to the present embodiment may estimate a schedule of the user on the basis of information acquired from a schedule application. Furthermore, the condition estimation unit 250 may estimate a schedule of the user by extracting a keyword related to a schedule from text information transmitted/received by the user in a message application or the like. Furthermore, the condition estimation unit 250 can estimate a schedule by extracting a keyword related to a schedule from a speech of the user.

Furthermore, the condition of the user according to the present embodiment may include a physical condition of the user. For example, the condition estimation unit 250 can estimate a physical condition of the user from a value of a body temperature included in sensor information collected by the information processing terminal 10. Furthermore, the condition estimation unit 250 may detect that the user visits a medical institution from collected GPS information and estimate a physical condition of the user. Furthermore, the condition estimation unit 250 can estimate a physical condition of the user from a speech, a cough, a sneeze, or the like of the user.

(Control Unit 260)

The control unit 260 has a function of determining, on the basis of an item to be improved which item is calculated by the health index calculation unit 210, an improving means to improve the item to be improved and a reward served in a case where the item to be improved is improved. Here, the control unit 260 according to the present embodiment may determine a reward related to an amusement favored by the user. Furthermore, the control unit 260 according to the present embodiment has a function of presenting contents of the determined improving means and reward to the user.

Moreover, the control unit 260 according to the present embodiment has a function of determining whether or not the item to be improved is improved on the basis of a variation in a health index successively calculated. Here, the control unit 260 makes a controlled object perform an operation corresponding to the above reward on the basis of the determination that the item to be improved is improved. According to the control unit 260 of the present embodiment, it becomes possible to encourage the user to voluntarily execute the improving means by using a desire for acquiring the reward.

Furthermore, the control unit 260 according to the present embodiment may have a function of calculating a degree of influence, on the health index, of the action by the user which action is estimated by the action estimation unit 230, and of determining an improving means on the basis of the degree of influence. Here, the control unit 260 can determine an improving means on the basis of the information stored in the action-index DB 240. For example, the control unit 260 may determine a more effective improving means on the basis of a value of a health index that varies when the user performs an action corresponding to the improving means.

Note that as described above, the improving means according to the present embodiment includes an action type and intensity of the action type. For example, in a case where an item to be improved is an amount of activity, the control unit 260 according to the present embodiment may determine an improving means in which an action type is designated as running and intensity is designated as 30 minutes. The control unit 260 may change the action type or intensity on the basis of a degree of influence of an action of the user on a health index. According to the control unit 260 of the present embodiment, an improving means corresponding to a characteristic of the user can be determined each time, and a higher health improvement effect can be expected. Note that the control unit 260 does not necessarily determine the above intensity. The control unit 260 may determine only an action type related to an improving means, and may present the action type to the user.

Furthermore, the control unit 260 according to the present embodiment may determine an improving means or reward on the basis of a condition of the user which condition is estimated by the condition estimation unit 250. As described above, the condition of the user according to the present embodiment includes a schedule, a physical condition, or the like of the user. According to the above function included in the control unit 260 of the present embodiment, it becomes possible to encourage a reasonable action change that fits more to every day of the user. Note that a detail and a detailed example of a function included in the control unit 260 according to the present embodiment will be separately described later.

(Presentation Unit 270)

The presentation unit 270 has a function of presenting contents of an improving means and reward on the basis of control by the control unit 260. Thus, the presentation unit 270 according to the present embodiment includes a display device to output visual information, a speaker to output sound information, or the like.

(Operation Unit 280)

The operation unit 280 has a function of performing an operation corresponding to reward on the basis of control by the control unit 260. Note that the operation unit 280 according to the present embodiment is realized by various devices corresponding to the reward determined by the control unit 260. A detailed example of the operation unit 280 according to the present embodiment will be separately described in detail.

(Communication Unit 290)

The communication unit 290 has a function of performing information communication with the information processing terminal 10 through the network 50. Specifically, the communication unit 290 receives sensor information from the information processing terminal 10. Furthermore, in a case where a controlled object by the control unit 260 is a device different from the information processing device 20, the communication unit 290 may transmit a control signal related to contents presentation of an improving means and reward or provision of the reward to the controlled object.

In the above, a functional configuration example of the information processing device 20 according to the present embodiment has been described. Note that the above functional configuration described with reference to FIG. 3 is just an example, and a functional configuration of the information processing device 20 according to the present embodiment is not limited to such an example. For example, each functional configuration included in the information processing device 20 may be separated into and realized by a plurality of devices. Furthermore, the information processing device 20 does not necessarily include all of the above-described configurations. For example, in a case where a controlled object by the control unit 260 is a device different from the information processing device 20, the information processing device 20 may not include the presentation unit 270 or the operation unit 280. On the one hand, the information processing device 20 according to the present embodiment can also perform control of both of the presentation unit 270 or the operation unit 280, and an external device. A functional configuration of the information processing device 20 according to the present embodiment may be modified arbitrarily according to a specification or operation.

1.5. Flow of Operation of Information Processing Device 20

Figure 4:
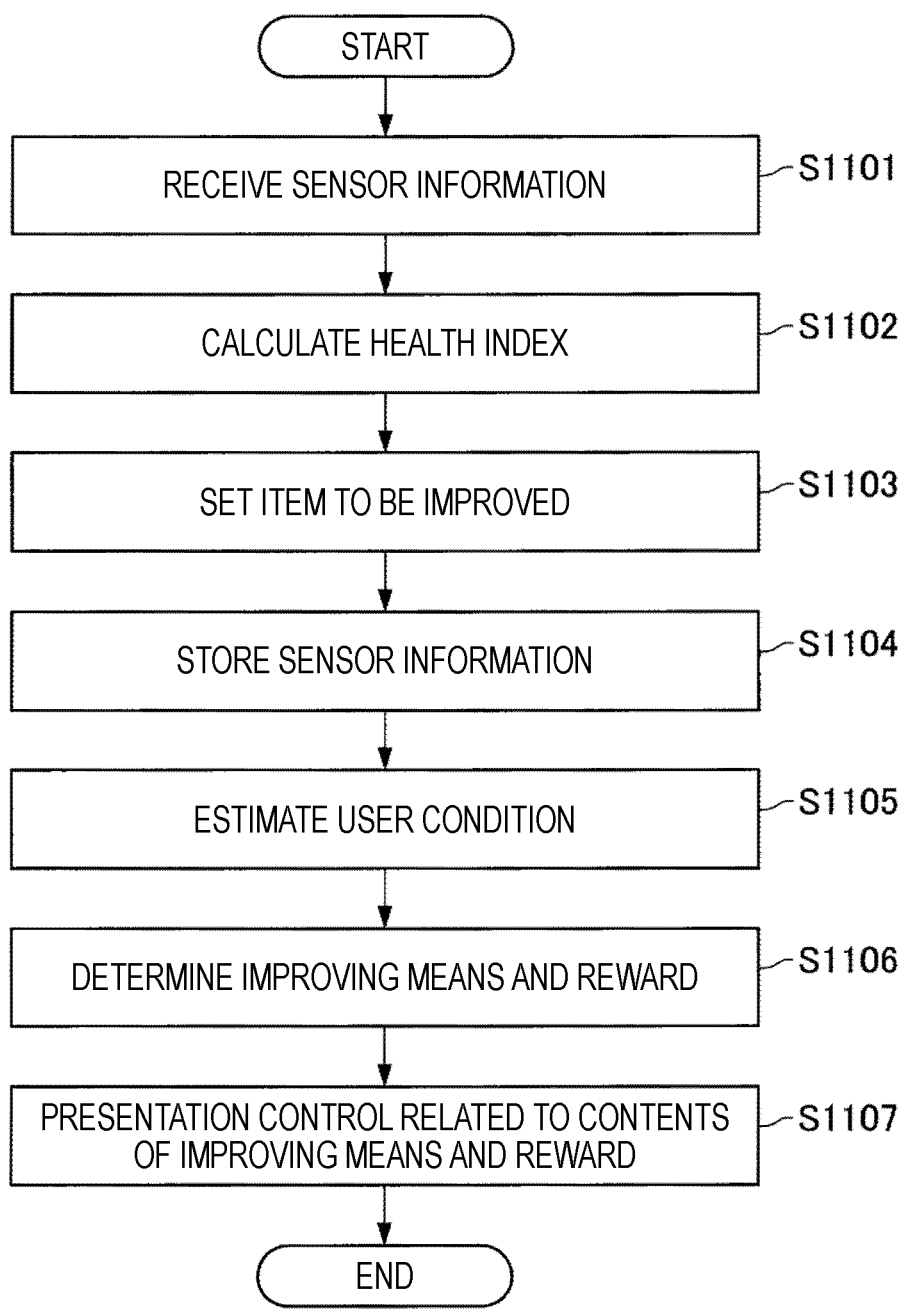
FIG. 4 is a flowchart illustrating a flow of determination and presentation control of an improving means and reward by the information processing device according to the embodiment.

Next, a flow of an operation of the information processing device 20 according to the present embodiment will be described. A flow of an operation of the information processing device 20 according to the present embodiment is briefly separated into two that are determination and presentation control of an improving means and reward, and determination whether or not there is improvement in an item to be improved after the presentation of the improving means and the reward and provision control of the reward. First, a flow of determination and presentation control of an improving means and a reward according to the present embodiment will be described. FIG. 4 is a flowchart illustrating a flow of determination and presentation control of an improving means and reward by the information processing device 20 according to the present embodiment.

As illustrated in FIG. 4, first, the communication unit 290 of the information processing device 20 receives sensor information from the information processing terminal 10 (S1101). Note that the sensor information received in step S1101 includes biological information of a user. Furthermore, the communication unit 290 may receive sensor information not only from the information processing terminal 10 but also from an imaging device or the like arranged around the user, for example.

Next, the health index calculation unit 210 calculates a health index on the basis of the sensor information received in step S1101 (S1102). Here, the health index calculation unit 210 first performs a noise removal with respect to the sensor information, a characteristic extraction corresponding to a kind of the sensor information, or the like. For example, in a case where the sensor information is pulse wave information, the health index calculation unit 210 may perform a drift removal by a high-pass filter, a beat interval calculation, or the like. Furthermore, in a case where the sensor information is perspiration information, the health index calculation unit 210 may perform downsampling, a deconvolution operation using an impulse response function, or the like. Furthermore, in a case where the sensor information is acceleration information, an operation using a moving average filter or the like may be performed. The health index calculation unit 210 can perform a highly-accurate health index on the basis of the sensor information processed in the above manner. For example, the health index calculation unit 210 can calculate a sympathetic activity level by applying an average filter for one minute after performing preprocessing or a characteristic extraction in the above manner with respect to the collected perspiration information.

Subsequently, the health index calculation unit 210 sets an item to be improved, the item requiring improvement, on the basis of the health index calculated in step S1102 (S1103). Here, the health index calculation unit 210 may set an item to be improved on the basis of a standard previously set for each item. For example, on the basis of the sympathetic activity level calculated in step S1102 being lower than the above standard, it is possible to set the sympathetic activity level as an item to be improved. Furthermore, as described above, the health index calculation unit 210 may set, as an item to be improved, an item with the largest difference from the determined standard among a plurality of calculated items.

Furthermore, the health index calculation unit 210 stores the sensor information received in step S1101 into the sensor DB 220 (S1104). The sensor information stored in step S1104 may be used later for learning by the health index calculation unit 210.

Next, the condition estimation unit 250 estimates a condition of the user on the basis of various kinds of acquired information or the sensor information received in step S1101 (S1105). For example, the condition estimation unit 250 may estimates a schedule of the user from information acquired from a schedule application or a message application, a speech of the user, or the like.

Next, the control unit 260 determines an improving means and reward on the basis of the item to be improved which item is set in step S1103 (S1106). Here, the control unit 260 may determine an improving means and reward on the basis further of the condition of the user which condition is estimated in step S1105.

Subsequently, the control unit 260 makes the presentation unit 270 or the like present contents of the improving means and the reward determined in step S1106 (S1107). Here, as described above, the control unit 260 can also make an external device or the information processing terminal 10 present the above contents.

Figure 5:
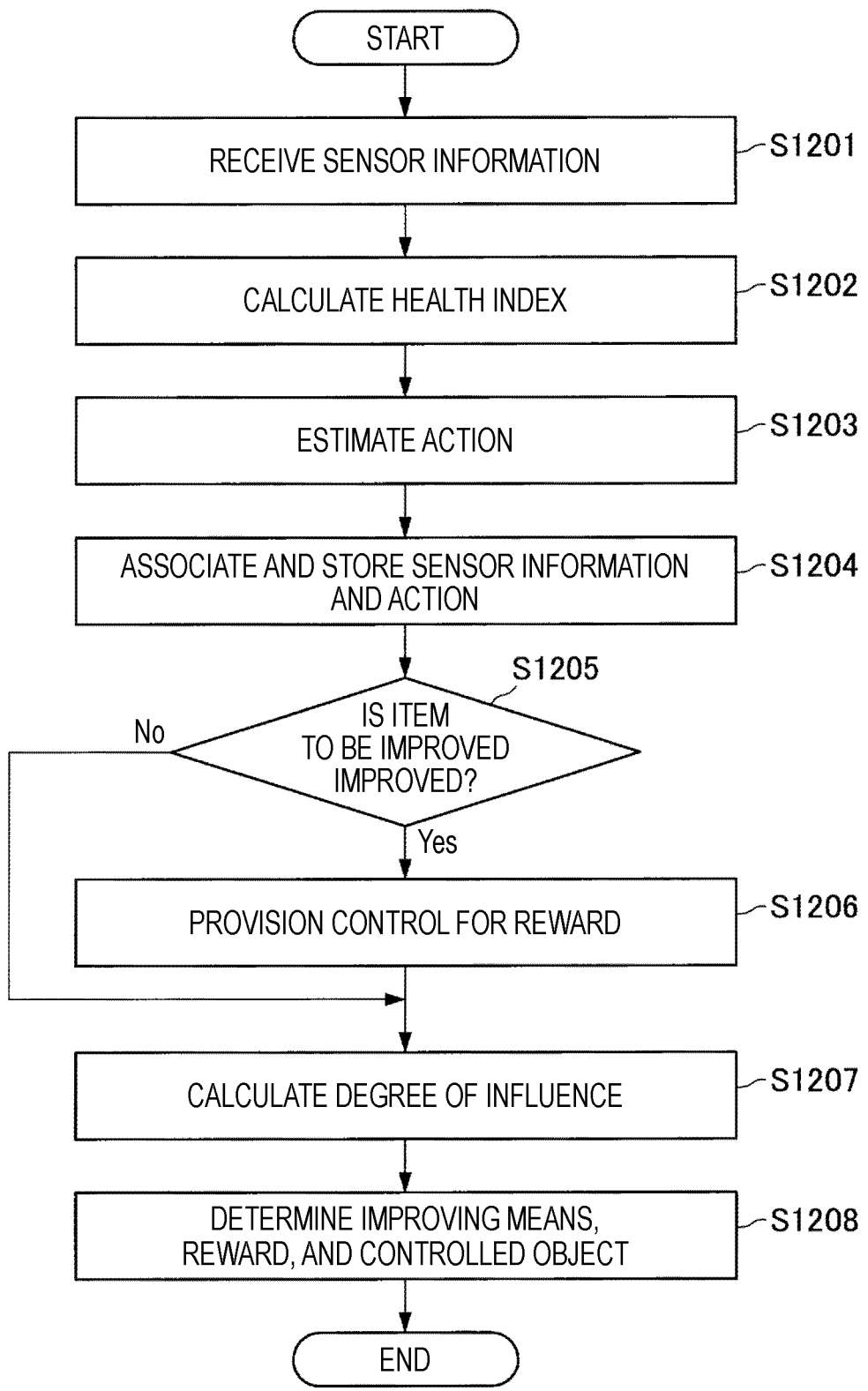
FIG. 5 is a flowchart illustrating a flow of determination whether or not there is improvement in an item to be improved and of provision of reward by the information processing device according to the embodiment.

In the above, a flow of determination and presentation control of an improving means and a reward according to the present embodiment has been described. Next, a flow of determination whether or not there is improvement in an item to be improved and of provision control of reward according to the present embodiment will be described. FIG. 5 is a flowchart illustrating a flow of determination whether or not there is improvement in an item to be improved and of provision of reward by the information processing device 20 according to the present embodiment.

As illustrated in FIG. 5, the communication unit 290 continuously receives sensor information from the information processing terminal 10 or the like after presentation of an improving means and reward (S1201).

Next, the health index calculation unit 210 calculates a health index on the basis of the sensor information received in step S1201 (S1202). Here, the health index calculation unit 210 calculates the same item as the health index calculated in step S1102 in FIG. 4.

Next, the action estimation unit 230 estimates an action of a user on the basis of the sensor information received in step S1201 (S1203). The action estimation unit 230 may estimate whether or not the user performs an action corresponding to an action type of an improving means, to which degree of intensity the action is performed, or the like.

Furthermore, the action estimation unit 230 makes the action-index DB 240 store the action estimated in step S1203 and the health index calculated in step S1202 in association (S1204).

Next, the control unit 260 determines whether or not the item to be improved which item is set in step S1103 in FIG. 4 is improved on the basis of the health index calculated in step S1202 (S1205).

Here, in a case of determining that the item to be improved is improved (S1205: Yes), the control unit 260 makes the operation unit 280 perform an operation corresponding to reward. In other words, the control unit 260 makes a controlled object provide reward (S1206).

On the one hand, in a case of determining that the item to be improved is not improved (S1205: No), the control unit 260 skips provision control of reward in step S1206.

Next, the control unit 260 calculates a degree of influence of the action, which is estimated in step S1203, on the health index (S1207). Here, the control unit 260 can calculate the above degree of influence on the basis of the information stored into the action-index DB 240 in step S1204.

Next, the control unit 260 determines a new improving means, reward, controlled object, and the like on the basis of the degree of influence calculated in step S1203 (S1208). Here, the control unit 260 may select, according to the determined reward, a controlled object to present the reward. According to the above function included in the control unit 260, it is possible to make various controlled objects provide a reward determined according to a characteristic or condition of a user, and it becomes possible to more flexibly encourage health improvement. Note that a detail of an operation of the control unit 260 in step S1208 will be described along with a detailed example in a description of examples described later.

1.6. First Example

In the above, functions included in the information processing terminal 10 and the information processing device 20 according to the present embodiment have been described. Next, examples of using the information processing terminal 10 and the information processing device 20 according to the present embodiment will be described.

First, a first example according to the present embodiment will be described. In the first example according to the present embodiment, a reward for advantageously progressing a game played by a user is provided in the game. In such a manner, an amusement according to the present embodiment includes a game, and a controlled object includes a game application.

Furthermore, an information processing terminal 10 according to the present example is, for example, a wristband-type wearable device, and an information processing device 20 may be a smartphone. Here, for example, a control unit 260 according to the present example may be one function of a game application. Note that the control unit 260 may be provided by being included in a software development kit (SDK) related to a game application.

Figure 6:
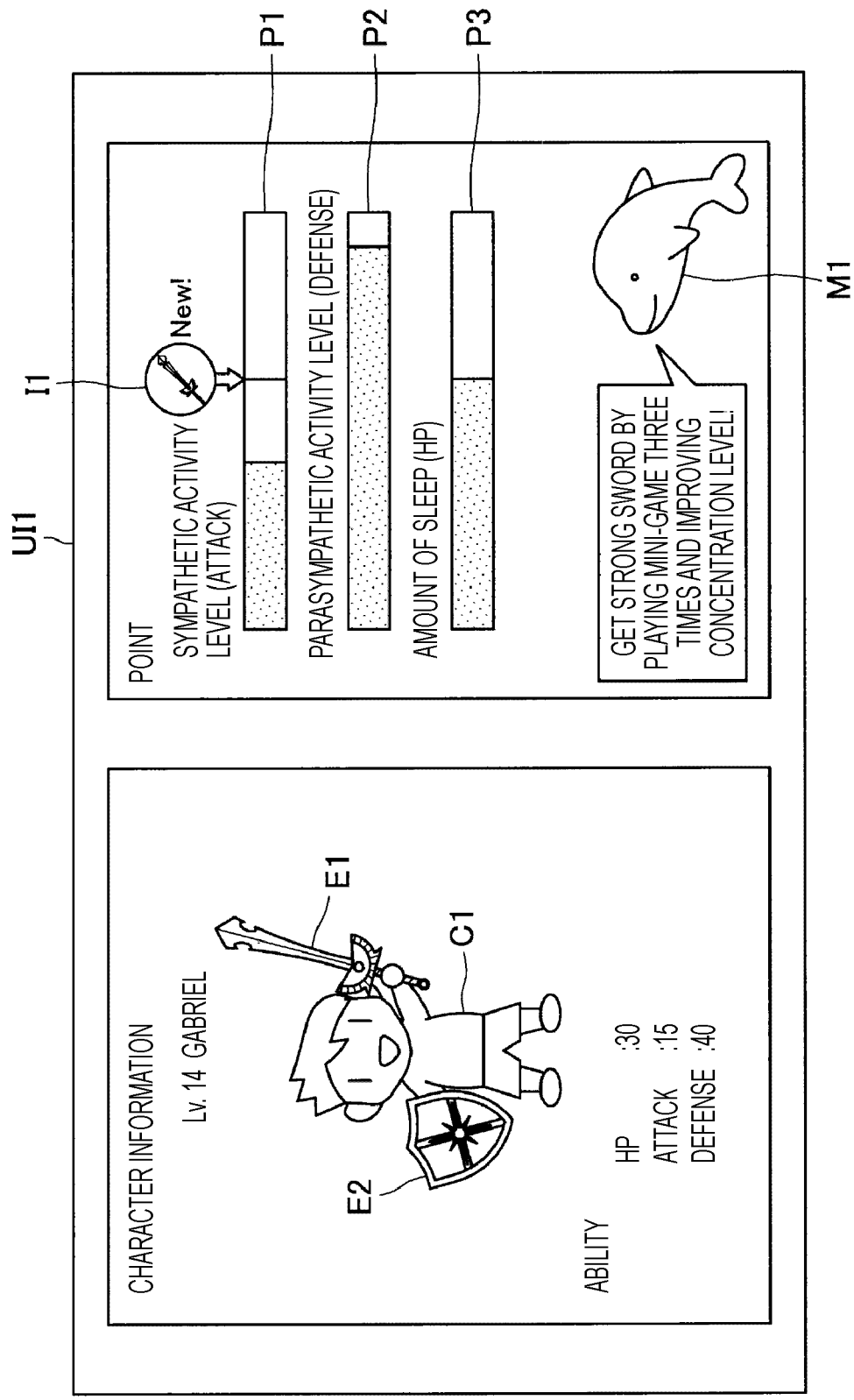
FIG. 6 is a view for describing an outline of a first example according to the embodiment.

FIG. 6 is a view for describing an outline of the present example. In FIG. 6, a user interface UI1 of a game application according to the present example is illustrated. For example, the user interface UI1 may be output by a presentation unit 270 of a smartphone.

Here, character information of a training object in a game application is displayed on a left side of the user interface UI1. In a case of one example illustrated in FIG. 6, graphics of a character C1 and equipment E1 and E2 of the character C1, status information, and the like are displayed.

Furthermore, items P1 to P3 related to a health index calculated by a health index calculation unit 210 are indicated by indicators on the left side of the user interface UI1. Here, each of the items P1 to 3 may correspond to the above status. In other words, a control unit 260 may determine a status of a training object in the game application on the basis of an item related to the health index calculated by the health index calculation unit 210.

Furthermore, in the one example illustrated in FIG. 6, a value of the item P1 indicating a sympathetic activity level is calculated to be low compared to the items P2 and P3. Thus, the health index calculation unit 210 according to the present embodiment may set, as an item to be improved, the item P1 indicating the sympathetic activity level.

Here, the control unit 260 according to the present example determines an improving means and reward on the basis of the item P1 indicating the sympathetic activity level that is the item to be improved. Furthermore, the control unit 260 makes the presentation unit 270 present contents of the determined improving means and reward. In a case of the one example illustrated in FIG. 6, the control unit 260 determines a mini-game to improve a concentration level as an improving means and new equipment applied to the character C1 as a reward, and makes the presentation unit 270 perform presentation. Specifically, the control unit 260 presents an action type of an improving means "mini-game", intensity "three times", and a reward "strong sword" through a mascot M1 in the game application. Furthermore, by adding an icon I1 to the item P1, the control unit 260 presents a degree of achievement of the item to be improved which degree is required for provision of the reward.

In such a manner, a reward according to the present embodiment may include a bonus related to enhancement of a training object in a game application, for example. According to the above presentation control by the control unit 260 of the present example, it is possible to encourage a user to execute an improving means by appealing to a desire for winning at a game.

Furthermore, in a case of estimating that an item to be improved is improved on the basis of a health index, which is calculated successively, after presentation of the improving means and the reward in the manner illustrated in FIG. 6, the control unit 260 makes an operation unit 280 perform an operation corresponding to the reward. In other words, the control unit 260 may make the operation unit 280 provide new equipment to the user in a case of the present example. Note that the operation unit 280 according to the present example may be one function of the game application in this case.

Furthermore, in a case where the item to be improved is improved, the control unit 260 may determine a new improving means and reward and make the presentation unit 270 perform presentation thereof. Here, the control unit 260 may calculate a degree of influence of the improving means on the health index and determine a new improving means on the basis of the degree of influence. As described above, the control unit 260 can calculate the above degree of influence on the basis of information recorded in an action-index DB 240.

Figure 7:
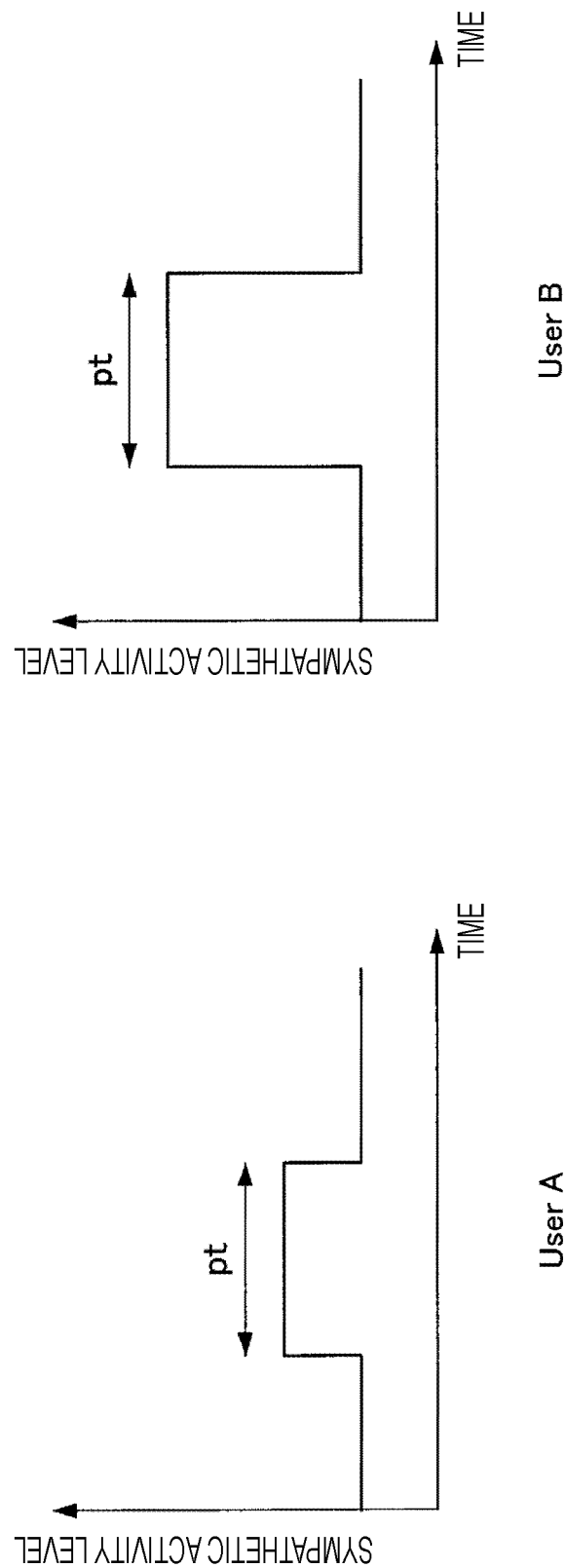
FIG. 7 is a graph for describing a degree of influence according to the embodiment.

FIG. 7 is a graph for describing a degree of influence according to the present embodiment. In FIG. 7, a degree of influence, on a sympathetic activity level, of an action of playing a mini-game to improve a degree of concentration is illustrated for each of a user A and a user B. Note that in the graph illustrated in FIG. 7, elapse of time is indicated in a horizontal axis and intensity of a sympathetic activity level is indicated in a vertical axis, and a period of playing the mini-game is indicated by an arrow pt. Furthermore, it is indicated in FIG. 7 that a degree of increase in the sympathetic activity level, that is, a degree of influence is higher in the user B than in the user A in a case where the same mini-game is played.

In such a manner, it is assumed that a degree of influence on a health index varies depending on a characteristic of a user even in a case where the same action is performed. Thus, for example, the control unit 260 may determine a next degree of achievement related to a health index in inverse proportion to the calculated degree of influence. In other words, the control unit 260 can set a higher degree of achievement in a case where the calculated degree of influence is high and can set a lower degree of achievement in a case where the calculated degree of influence is low.

According to the above function included in the control unit 260, it can be expected that a variation in progress in a game, the progress depending on a difference in a degree of influence between users, is controlled and reduction in energy of a user to execute an improving means is controlled. Furthermore, the control unit 260 may determine that a current improving means is not effective for a user and set an improving means again in a case where the degree of influence is lower than a threshold. Here, the control unit 260 may change an action type related to an improving means or may increase a degree of influence on a health index by increasing intensity.

Figure 8:
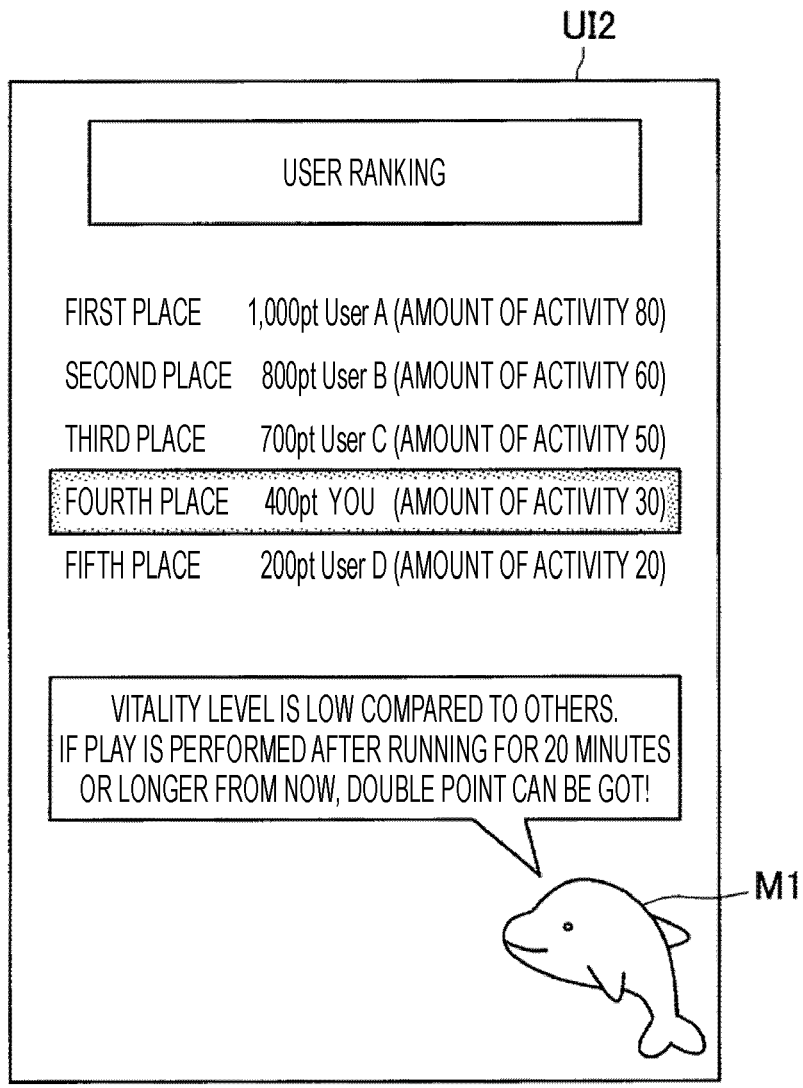
FIG. 8 is a view for describing an item to be improved and reward that are determined on the basis of a health index of a different user according to the embodiment.

Furthermore, in a case where a controlled object according to the present embodiment is a game application or the like in which a plurality of users participates, the health index calculation unit 210 may set an item to be improved on the basis of a health index of a different user in the application. Furthermore, here, the control unit 260 can determine a reward on the basis of a health index of a different user. FIG. 8 is a view for describing an item to be improved and a reward that are determined on the basis of a health index of a different user.

In FIG. 8, a user interface UI2 of a game application is illustrated, and a user ranking in the game application is displayed on the user interface UI2. Furthermore, a point in the game application, a user name, and an amount of activity calculated by the health index calculation unit 210 are indicated in the above user ranking.

In a case of one example illustrated in FIG. 8, on the basis of an amount of activity of a user corresponding to "you" in FIG. 6 being relatively low compared to an amount of activity of a different user, the health index calculation unit 210 sets the amount of activity as an item to be improved. Furthermore, the control unit 260 determines an improving means and reward on the basis of the above item to be improved which item is set by the health index calculation unit 210. Specifically, the control unit 260 presents an action type of an improving means "running", intensity "20 minutes", and a reward "double point" to a user through the mascot M1. According to the above function included in the control unit 260 of the present embodiment, it is possible to encourage a user to execute an improving means by appealing to a desire for beating the others or for not becoming inferior to the others.

Figure 9:
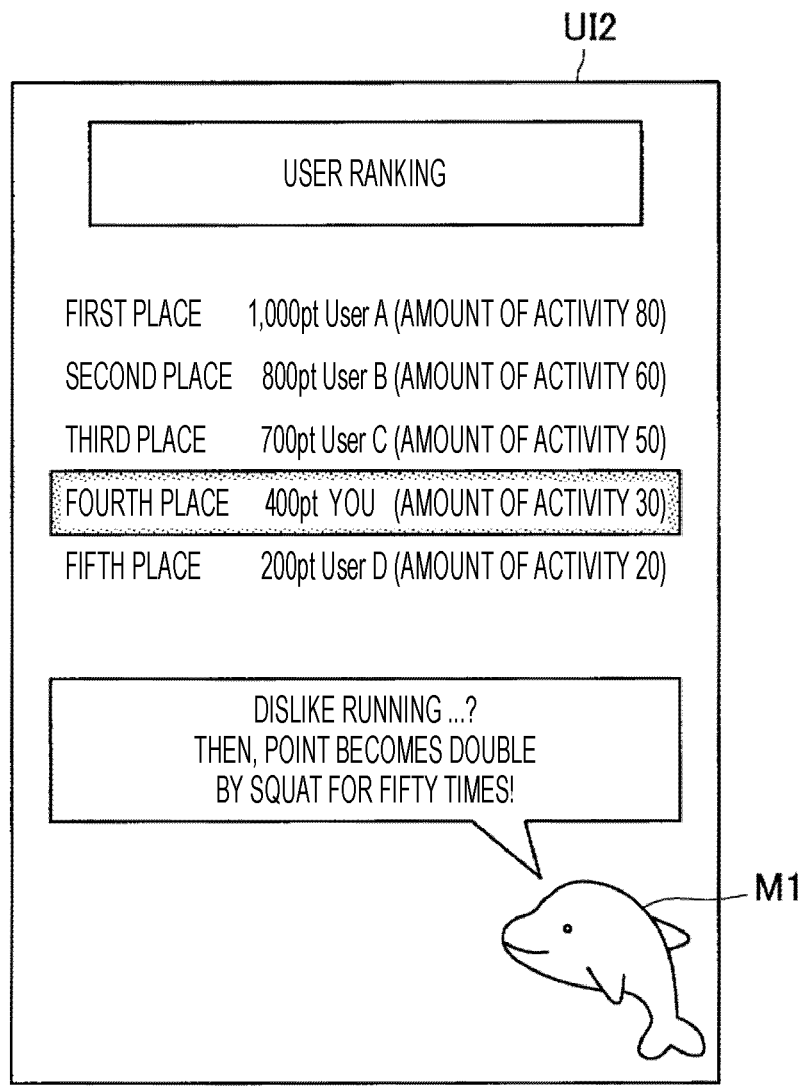
FIG. 9 is a view for describing an improving means that is changed on the basis of non-performance of an action corresponding to an action type according to the embodiment.

Furthermore, the control unit 260 according to the present embodiment may change an improving means or reward on the basis of non-performance, by a user, of an action corresponding to an action type of an improving means. FIG. 9 is a view for describing an improving means changed on the basis of non-performance of an action corresponding to an action type. Similarly to FIG. 8, a user interface UI2 of a game application is illustrated in FIG. 9. On the one hand, in comparison between FIG. 9 and FIG. 8, an improving means different from that in FIG. 8 is presented through a mascot M1 in FIG. 9.

Specifically, in a case of one example illustrated in FIG. 9, on the basis of non-performance, by a user, of the action type "running" presented in FIG. 8, the control unit 260 determines a new action type "squat" and intensity "50 times" and makes the presentation unit 270 perform presentation thereof. In such a manner, in a case where the user does not make an action corresponding to an action type, the control unit 260 according to the present embodiment can determine that a burden of the action type is heavy for the user, and can make a change to a different improving means.

Furthermore, on the one hand, the control unit 260 can encourage the user to execute an improving means by changing reward without changing the improving means. In this case, the control unit 260 may increase energy of the user by presenting a reward more appealing to the user. In such a manner, according to the control unit 260 of the present embodiment, it is possible to set an improving means with a less execution burden or a more appealing reward according to a user, and to more effectively guide the user.

Figure 10:
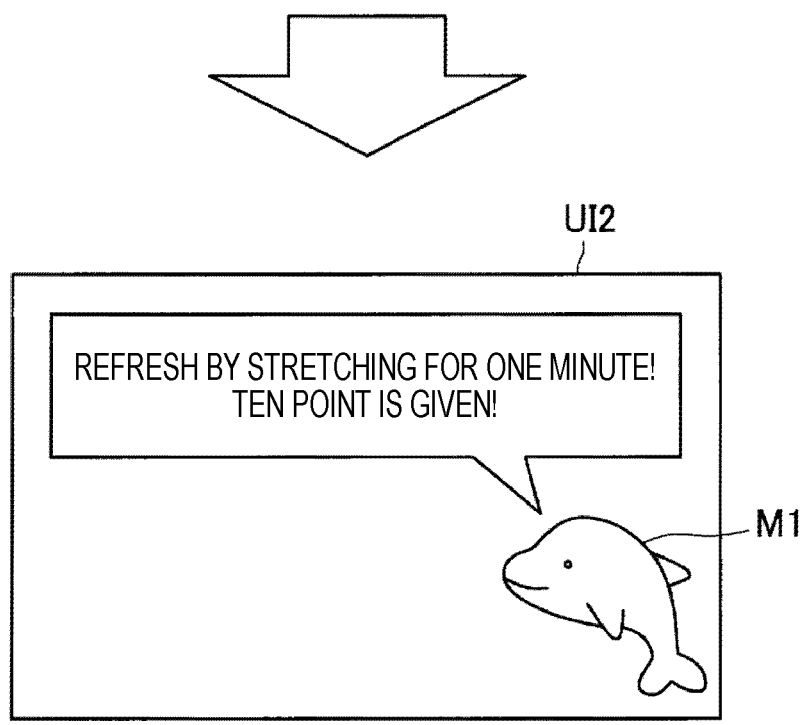
FIG. 10 is a view for describing an improving means and reward that are determined on the basis of a condition of a user according to the embodiment.

Furthermore, as described above, the control unit 260 according to the present embodiment may determine an improving means or reward on the basis of a condition of the user which condition is estimated by a condition estimation unit 250. FIG. 10 is a view for describing an improving means and a reward determined on the basis of a condition of a user.

A schedule of the user which schedule is estimated by the condition estimation unit 250 is illustrated in an upper part of FIG. 10. For example, the condition estimation unit 250 can estimate a schedule of the user on the basis of information acquired from a schedule application or a message application, a speech of the user, or the like.

Here, in a case where current time is five in the evening, it is estimated that the user is working. Here, as illustrated in a lower part of FIG. 10, the control unit 260 according to the present embodiment may determine an easy action type "stretching", intensity "one minute", or the like that can be performed even during the work. Furthermore, the control unit 260 can determine an appropriate reward "10 points" corresponding to the determined improving means. In such a manner, according to the control unit 260 of the present embodiment, it is possible to set an improving means or reward each time according to a condition of a user and it becomes possible to encourage health improvement that fits more to daily life of the user.

Note that in FIG. 10, an example in which the control unit 260 determines an improving means and reward on the basis of a schedule of the user has been described. However, the control unit 260 may determine an improving means or reward on the basis of an estimated physical condition of the user. In this case, in a case where it is estimated that a physical condition of the user is not well, the control unit 260 determines an improving means with a less burden. On the one hand, in a case where it is estimated that a physical condition of the user is well, the control unit 260 may determine an improving means with a burden heavier than usual.

1.7. Second Example

Next, a second example according to the present embodiment will be described. In the above first example, a case where the information processing device 20 determines a reward that can be used in a game application, and controls provision or the like of the reward has been described as an example. On the one hand, in the second example according to the present embodiment, an information processing device 20 may determine available time for a game application, a browser application, or the like as a reward and may control provision or the like of the reward.

For example, in a case where a lack of sunlight is set as an item to be improved on the basis of a health index calculated by a health index calculation unit 210, a control unit 260 according to the present example can perform control of extending available time of a game application, a browser application, or the like on the basis of improvement in the item to be improved by exposure of a user to sunlight outside.

Figure 11:
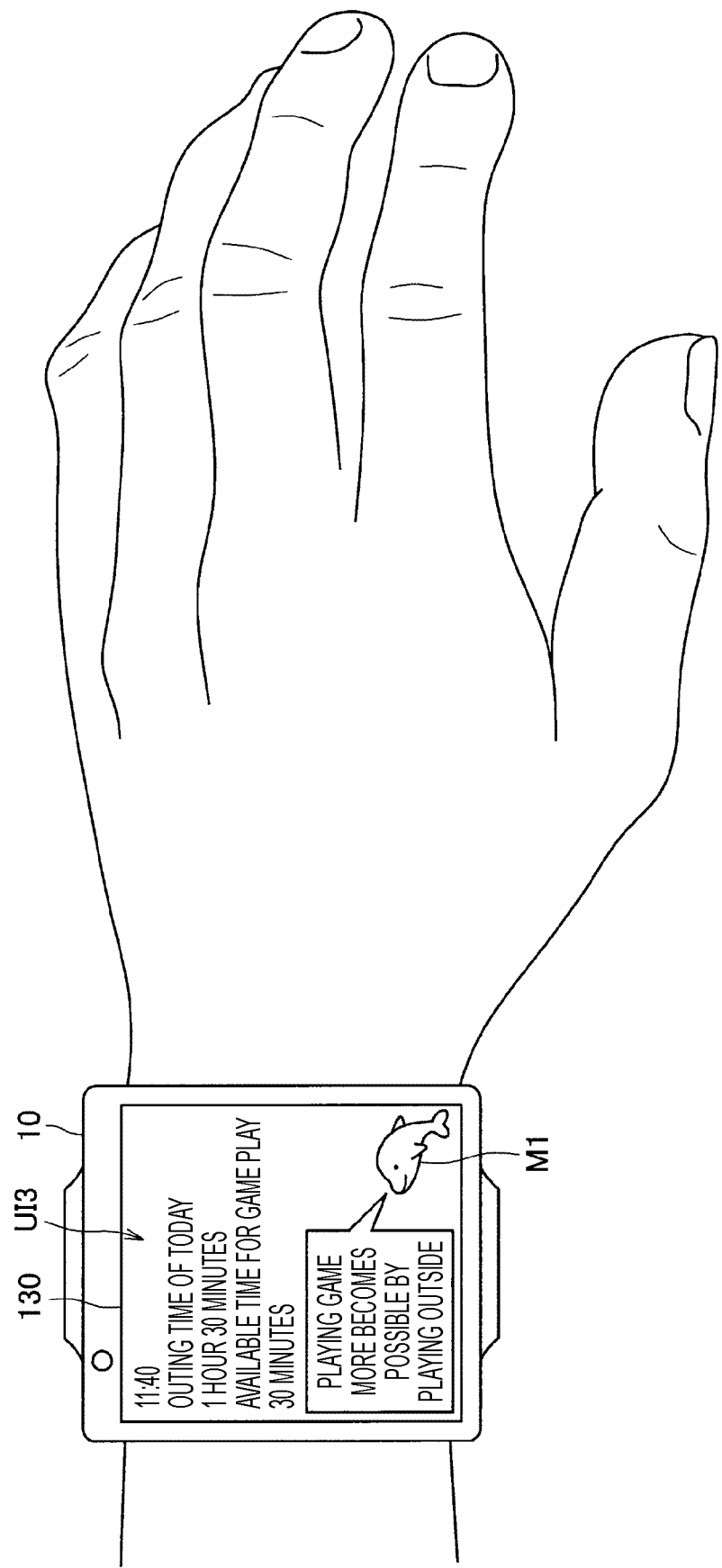
FIG. 11 is a view for describing an outline of a second example according to the embodiment.

FIG. 11 is a view for describing an outline of the second example according to the present embodiment. In FIG. 11, an example of a case where the information processing device 20 calculates a health index and determines improvement in an item to be improved, that is, a lack of sunlight on the basis of illuminance information (ultraviolet information) or GPS information collected by a wristband-type wearable device the user wears is illustrated.

Here, for example, the information processing device 20 may display present outing time or available time for a game on a user interface U13 displayed on an output unit 130 of an information processing terminal 10. Furthermore, in a case of the one example illustrated in FIG. 11, the information processing device 20 presents a user an improving means "playing outside" and a reward "game can be played" through a mascot M1. In such a manner, according to the information processing device 20 of the present example, it is possible to effectively encourage health improvement of a user by appealing, specifically, to a desire of a child user for playing game or performing browsing longer.

1.8. Third Example

Next, a third example according to the present embodiment will be described. An information processing device 20 according to the third example may set a lack of social knowledge of a user as an item to be improved on the basis of a calculated health index, and determine increasing an intelligence level of a pet-type robot as a reward provided in a case where the lack of social knowledge is improved. In such a manner, a health index according to the present embodiment may include social health.

Figure 12:
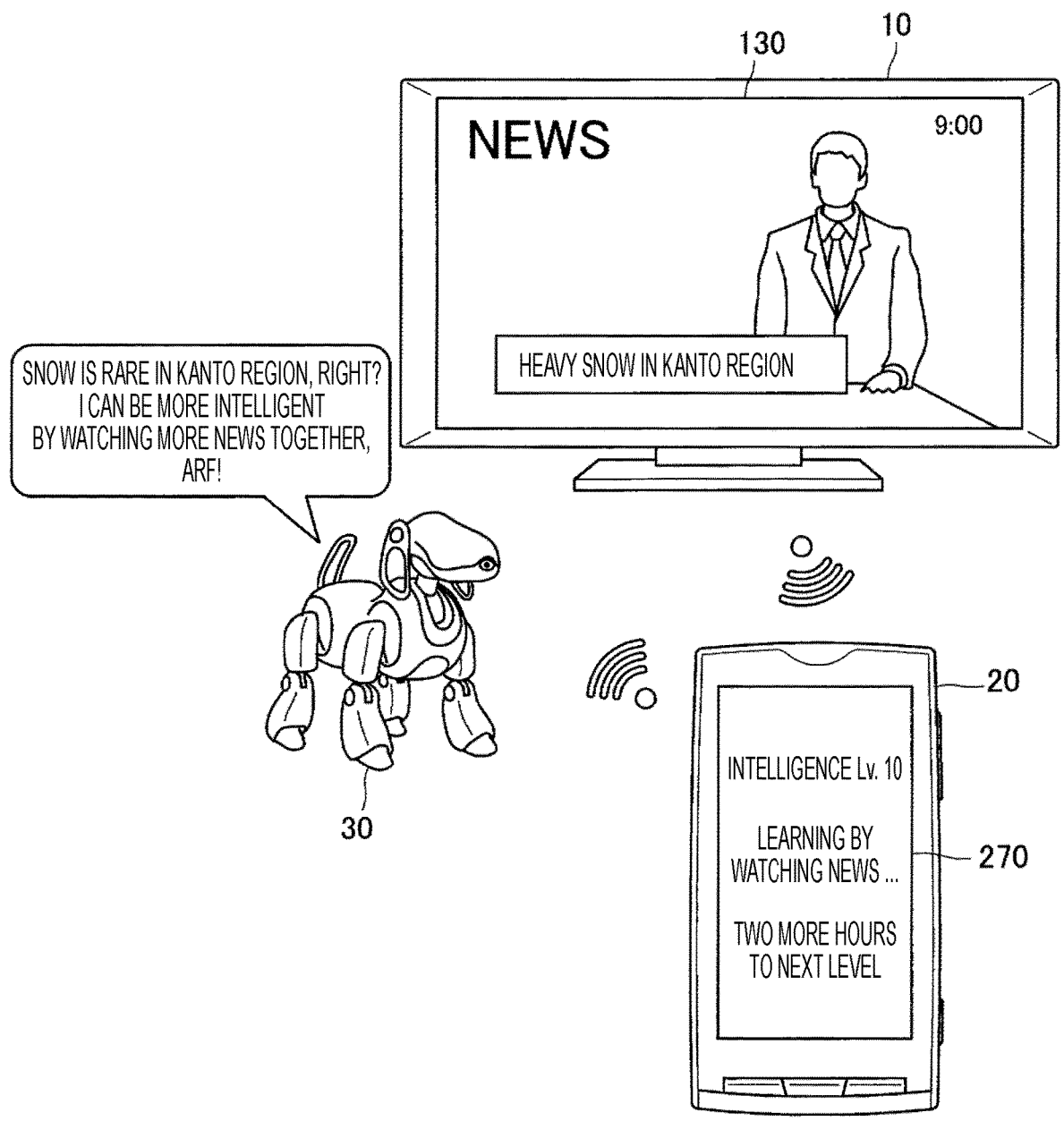
FIG. 12 is a view for describing an outline of a third example according to the embodiment.

FIG. 12 is a view for describing the third example according to the present embodiment. An information processing device 20 according to the present example can detect that a browsing action of a user is weighted in browsing of contents related to a hobby and that browsing time related, for example, to social knowledge such as news is shorter than a threshold through a television-type information processing terminal 10 or a plug-in introduced in the information processing device 20, for example.

Here, the information processing device 20 according to the present example sets a lack of social knowledge as an item to be improved, and presents a user that an intelligence level of a controlled object 30 that is a pet-type robot is increased in a case where the item to be improved is improved. Specifically, as illustrated in FIG. 12, the information processing device 20 may make a presentation unit 270 or the controlled object 30 present an action type "watching news", intensity "two hours", and a reward "becoming intelligent".

According to the information processing device 20 of the present example, it becomes possible to encourage health improvement of a user by appealing to a desire for raising the controlled object 30, which is a pet-type robot, more intelligent.

1.9. Fourth Example

Next, a fourth example according to the present embodiment will be described. An information processing device 20 according to the fourth example may set a lack of sleep of a user as an item to be improved on the basis of a calculated health index and may determine giving water or light to a plant raised by the user as a reward provided in a case where the lack of sleep is improved.

Figure 13:
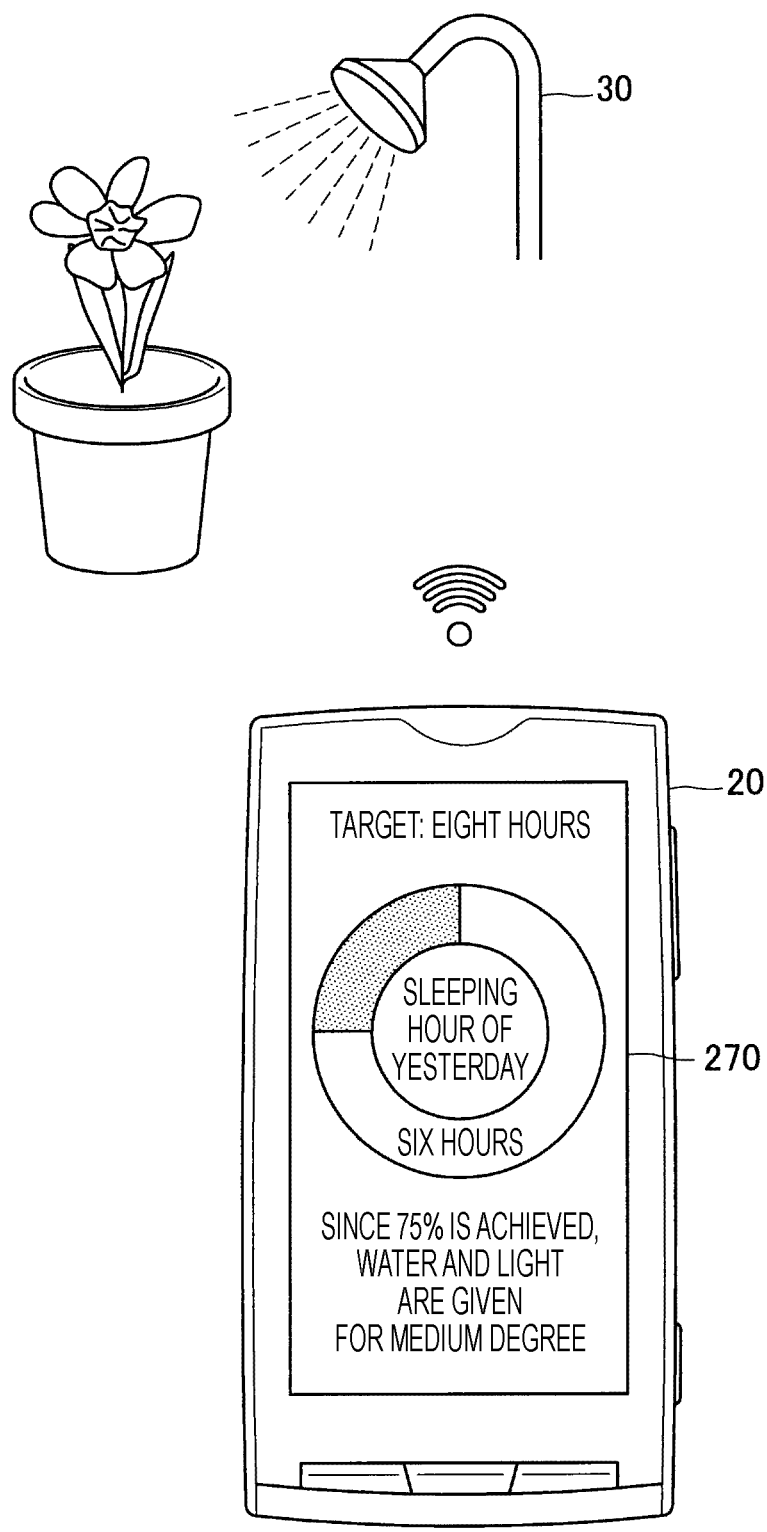
FIG. 13 is a view for describing an outline of a fourth example according to the embodiment.

FIG. 13 is a view for describing the fourth example according to the present embodiment. For example, on the basis of pulse wave information or the like collected by an information processing terminal 10 that a user wears, the information processing device 20 according to the present example can derive an HF component that becomes an index of a parasympathetic activity level, and calculate an amount of sleep by integration of time in which a value of the HF component exceeds a threshold. Here, a health index calculation unit 210 may set the amount of sleep as an item to be improved on the basis of the amount of sleep being lower than a threshold. Furthermore, a control unit 260 can make a presentation unit 270 present an action type of an improving means "sleep" or intensity "eight hours".

Furthermore, the control unit 260 can make a controlled object 30 provide a reward "giving water and light" on the basis of sensor information collected by the information processing terminal 10. In a case of the one example illustrated in FIG. 13, the control unit 260 makes the controlled object 30 provide a reward for a medium degree on the basis of sleeping hours of a user achieving 75% of intensity. In such a manner, the control unit 260 according to the present embodiment may make the controlled object 30 provide a reward corresponding to a degree of improvement even in a case where an item to be improved is not improved completely.

According to the information processing device 20 of the present example, it becomes possible to encourage health improvement of a user by appealing to a desire for growing a grown plant or the like more beautifully.

1.10. Fifth Example

Next, a fifth example according to the present embodiment will be described. An information processing device 20 according to the fifth example may set a posture of a user as an item to be improved on the basis of a calculated health index and determine provision of an image favored by the user as a reward provided in a case where a bad posture is improved.

Figure 14:
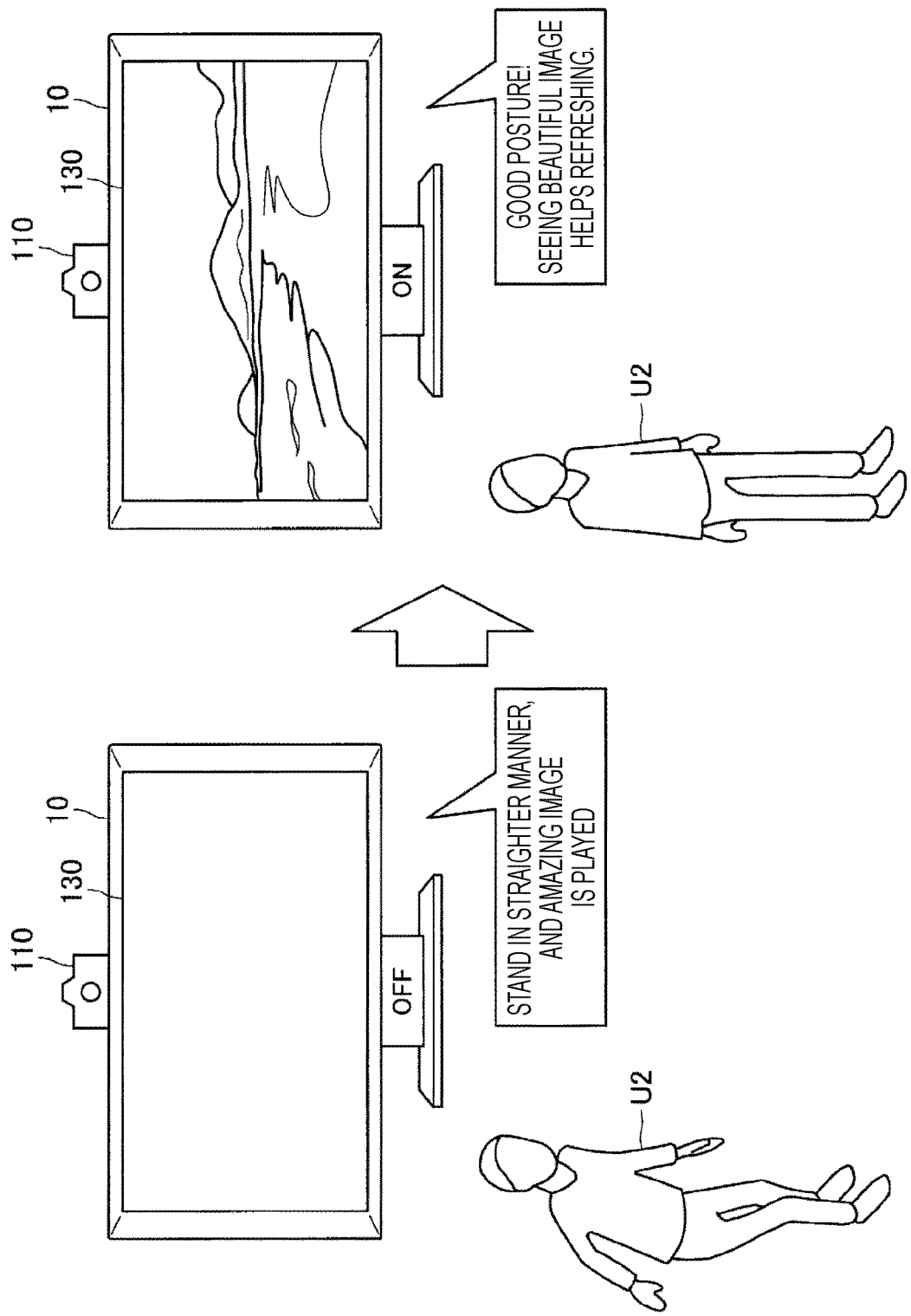
FIG. 14 is a view for describing an outline of a fifth example according to the embodiment.

FIG. 14 is a view for describing an outline of the fifth example according to the present embodiment. The information processing device 20 according to the present example may set a bad posture of a user U2 as an item to be improved on the basis of image information collected by a sensor unit 110 of a television-type information processing terminal 10, for example. Furthermore, here, the information processing device 20 may make an output unit 130 of the information processing terminal 10 present an improving means "standing straight" and a reward "amazing image".

Furthermore, in a case of determining that the bad posture of the user U2 is improved on the basis of image information collected by the information processing terminal 10, the information processing device 20 can make the output unit 130 of the information processing terminal 10 play a moving image corresponding to the reward "amazing image".

According to the information processing device 20 of the present example, it becomes possible to encourage health improvement of a user by appealing to a mind of the user who likes a beautiful image.

1.11. Sixth Example

Next, a sixth example according to the present embodiment will be described. For example, an information processing device 20 according to the sixth example may set insufficient blushing of teeth of a user as an item to be improved on the basis of a calculated health index and determine provision of an image favored by the user as a reward provided in a case where the insufficient blushing of teeth is improved.

Figure 15:
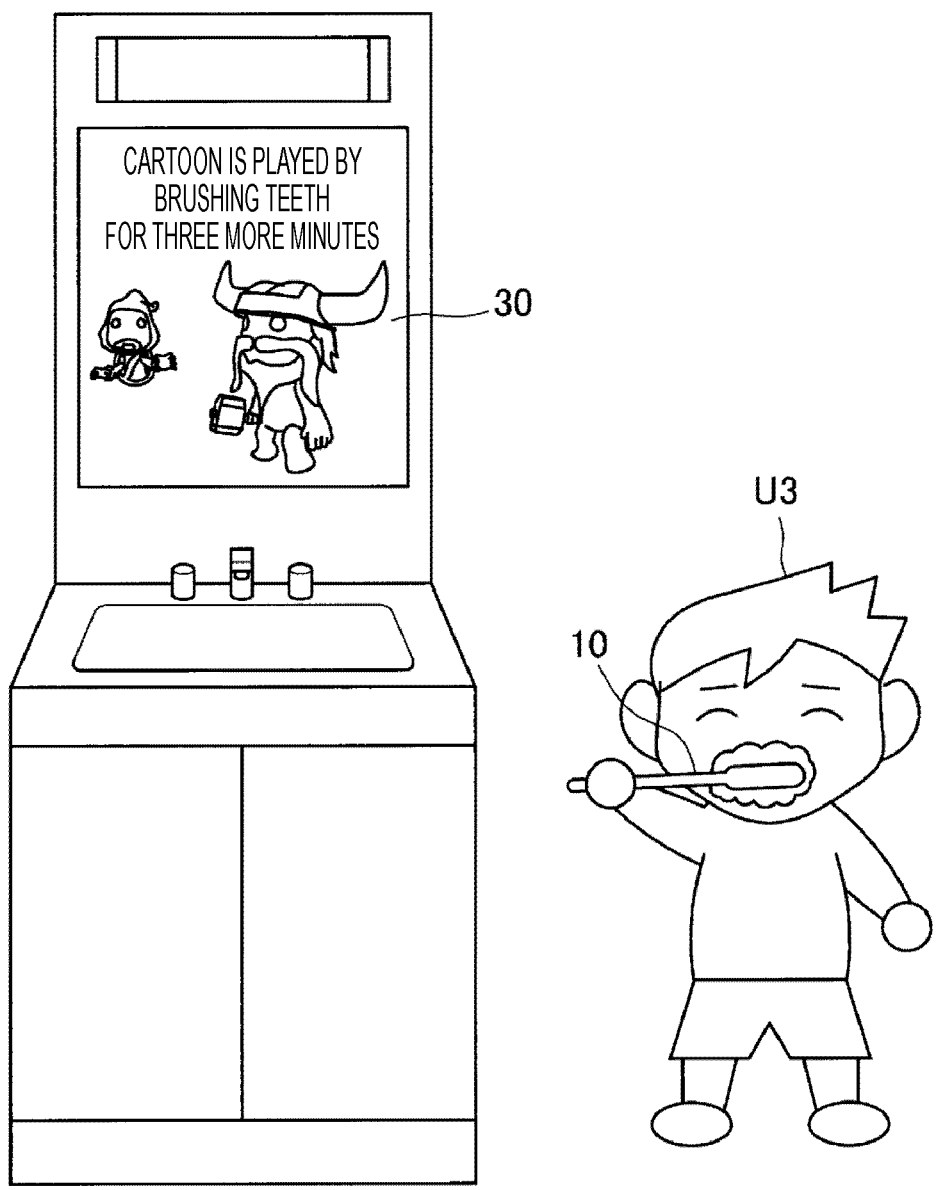
FIG. 15 is a view for describing an outline of a sixth example according to the embodiment.

FIG. 15 is a view for describing an outline of the sixth example according to the present embodiment. For example, the information processing device 20 according to the present example may set insufficient blushing of teeth of a user U3 as an item to be improved on the basis of acceleration information collected by a toothbrush-type information processing terminal 10. Furthermore, here, the information processing device 20 may present an action type "blushing teeth", intensity "three minutes", and a reward "playing a cartoon" on a display embedded in a mirror of a sink-type controlled object 30.

Furthermore, in a case of determining that the insufficient blushing of teeth of the user U3 is solved on the basis of acceleration information collected by the toothbrush-type information processing terminal 10, the information processing device 20 can make the sink-type controlled object 30 play a cartoon corresponding to the reward.

According to the information processing device 20 of the present example, it becomes possible to encourage health improvement of a user by appealing, specifically, to a desire of a child user for watching a cartoon.

1.12. Seventh Example

Next, a seventh example according to the present embodiment will be described. For example, an information processing device 20 according to the seventh example may set a lack of communication of a user as an item to be improved on the basis of a calculated health index, and determine improvement in a speech frequency or a language learning function of a pet-type robot as a reward provided in a case where the lack in communication is improved.

FIG. 16 is a view for describing an outline of the seventh example according to the present embodiment. For example, the information processing device 20 according to the present example may set a lack in communication of a user U4 as an item to be improved on the basis of speech information of the user U4 which information is collected by an information processing terminal 10 that is a pet-type robot. Furthermore, here, the information processing device 20 may suggestively indicate an item to be improved by not making the information processing terminal 10, which is a pet-type robot, make a speech.

Furthermore, in a case of determining that the lack of communication of the user U4 is improved on the basis of the speech information of the user U4 which information is collected by the information processing terminal 10 that is a pet-type robot, the information processing device 20 can make the information processing terminal 10 perform learning or an output using a synthetic sound according to speech contents of the user U4.

According to the information processing device 20 of the present example, it becomes possible to effectively improve a lack of communication or the like in a family by appealing to a desire of a user for letting the pet-type robot make a more fulfilling speech, for example.

1.13. Eighth Example

Next, an eighth example according to the present embodiment will be described. For example, an information processing device 20 according to the eighth example may set a lack of an amount of activity of a user as an item to be improved on the basis of a calculated health index, and determine an effective navigation route in a theme park or the like as a reward.

Figure 17:
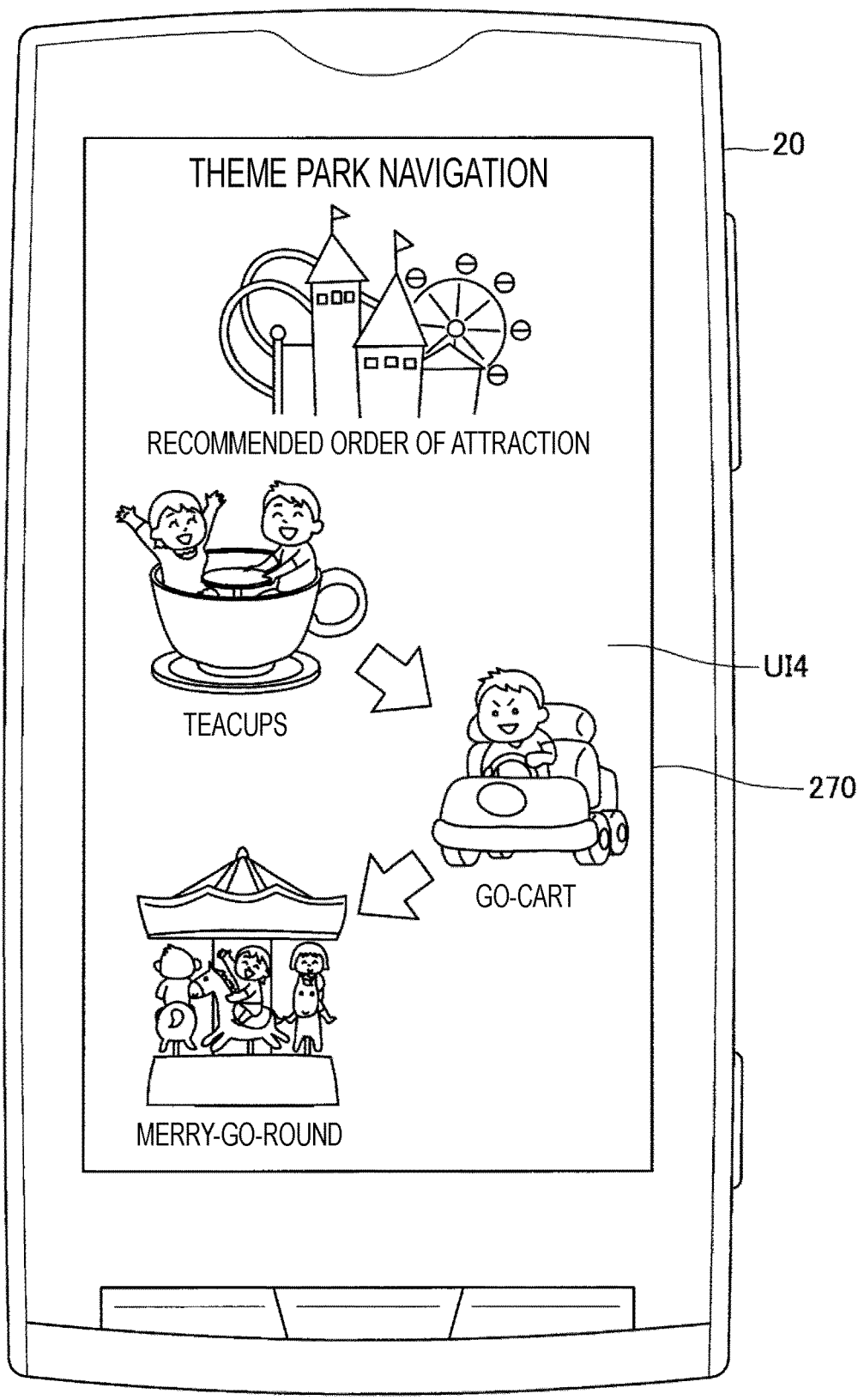
FIG. 17 is a view for describing an outline of an eighth example according to the embodiment.

FIG. 17 is a view for describing an outline of the eighth example according to the present embodiment. For example, the information processing device 20 according to the present example may set a lack of an amount of activity of a user as an item to be improved on the basis of acceleration information or GPS information collected by an information processing terminal 10 held by the user. Furthermore, as illustrated in FIG. 17, by controlling an application of performing navigation in a theme park, the information processing device 20 can present recommended utilization order of facilities in the park onto a user interface UI4. Here, the information processing device 20 may determine the above recommended utilization order on the basis of prediction of the congestion concrete or waiting time related to the facilities in the park.

In such a manner, according to the information processing device 20 of the present example, by appealing to a desire of a user for enjoying as many facilities as possible in the park, it is possible to increase an amount of activity of a user which activity is associated with a movement between facilities in the park.

1.14. Ninth Example

Next, a ninth example according to the present embodiment will be described. For example, the information processing device 20 according to the ninth example may set insufficient mastication of a user as an item to be improved on the basis of a calculated health index, and determine a bonus in a game application as a reward provided in a case where the insufficient mastication is improved.

Figure 18:
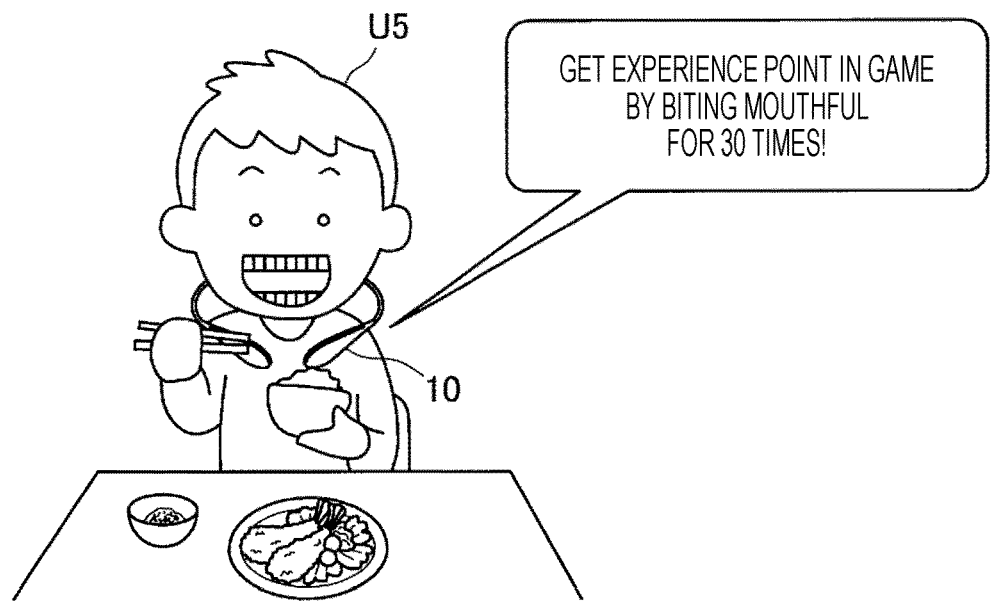
FIG. 18 is a view for describing an outline of a ninth example according to the embodiment.

FIG. 18 is a view for describing an outline of the ninth example according to the present embodiment. For example, the information processing device 20 according to the present example may detect mastication or deglutition of a user U5 on the basis of acceleration information or angular velocity information collected by an information processing terminal 10, which is a neckband-type wearable device, and set the number of times of mastication as an item to be improved. Furthermore, here, the information processing device 20 may make the information processing terminal 10, which is a neckband-type wearable device, present an action type "biting", intensity "30 times", and a reward "an experience point".

Furthermore, in a case of determining that the insufficient mastication of the user U5 is improved on the basis of the acceleration information or the angular velocity information collected by the information processing terminal 10 that is a neckband-type wearable device, the information processing device 20 can make a game application, which is a controlled object, give an experience point corresponding to the reward.

According to the information processing device 20 of the present example, it becomes possible to encourage health improvement of a user by appealing to a desire of the user for progressing a game with advantage.

1.15. Tenth Example

Next, a tenth example according to the present embodiment will be described. For example, an information processing device 20 according to the tenth example may set quality of sleep of a user as an item to be improved on the basis of a calculated health index, and determine a bonus in a game application as a reward provided in a case where the quality of sleep is improved.

Figure 19:
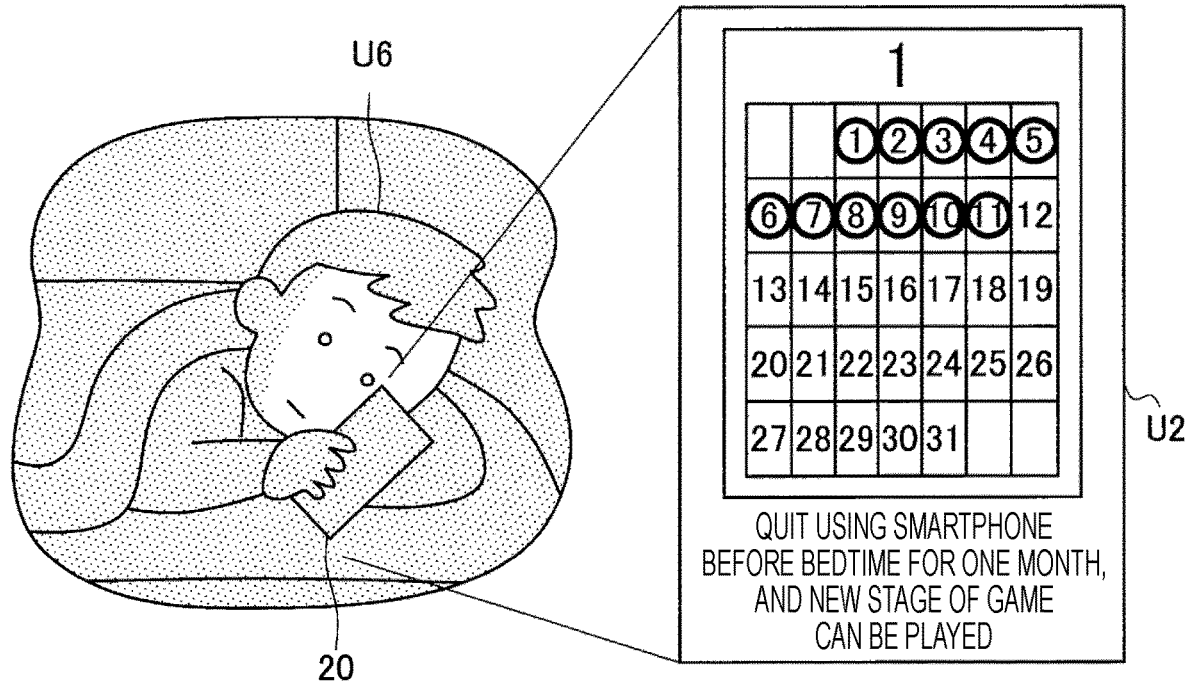
FIG. 19 is a view for describing an outline of a tenth example according to the embodiment.

FIG. 19 is a view for describing an outline of the tenth example according to the present embodiment. For example, the information processing device 20 according to the present example may set quality of sleep of a user U6 as an item to be improved on the basis of acceleration information collected by an information processing terminal 10 that is a wristband-type wearable device. Furthermore, here, a smartphone-type information processing device 20 may make a presentation unit 270 or the like present an action type "smartphone operation before going to bed", intensity "one month", and a reward "a new stage of a game can be played".

On the basis of collected illuminance information indicating darkness equal to or lower than a threshold or angular velocity information indicating that a direction of the smartphone-type information processing device 20 is straight to a direction of gravity, the information processing device 20 can detect whether or not there is operation on a smartphone and perform determination of an item to be improved. Furthermore, the information processing device 20 may make a game application, which is a controlled object, release a new stage on the basis of not detecting smartphone operation of a sleeping eye for a month.

According to the information processing device 20 of the present example, it becomes possible to encourage health improvement of a user by appealing to a desire of the user for playing a new game.

1.16. Eleventh Example

Next, an eleventh example according to the present embodiment will be described. For example, an information processing device 20 according to the eleventh example may set too much sleep of a user as an item to be improved on the basis of a calculated health index, and may determine playing music as a reward provided in a case where the too much sleep is improved.

FIG. 20 is a view for describing an outline of the eleventh example according to the present embodiment. For example, the information processing device 20 according to the present example may detect an act of going back to sleep of a user U7 on the basis of acceleration information collected by an information processing terminal 10 that is a wristband-type wearable device, and may set too much sleep as an item to be improved. Furthermore, here, the information processing device 20 may make the information processing terminal 10, a controlled object 30, or the like present an action type "not going back to sleep" or a reward "playing a new song".

Furthermore, the information processing device 20 can make the controlled object 30 play a new song in a case of determining that the going back to sleep is improved on the basis of the acceleration information collected by the information processing terminal 10 that is a wristband-type wearable device.

According to the information processing device 20 of the present example, it becomes possible to encourage health improvement of a user by appealing to a mind of the user who likes music.

1.17. Twelfth Example

Next, a twelfth example according to the present embodiment will be described. For example, an information processing device 20 according to the twelfth example can present a user an action to improve a mental state by setting a mental state of the user as an item to be improved on the basis of a calculated health index.

Figure 21:
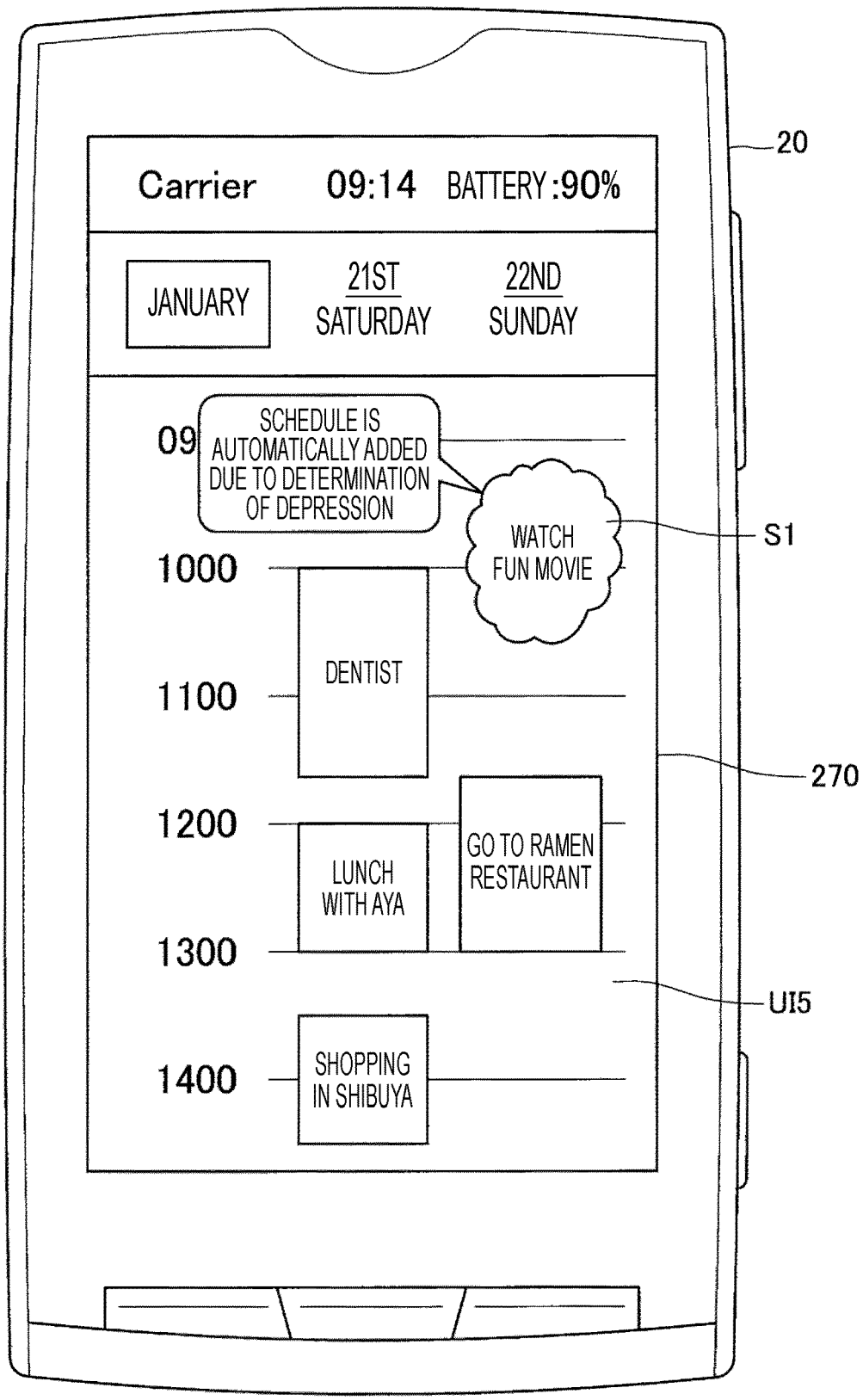
FIG. 21 is a view for describing an outline of a twelfth example according to the embodiment.

FIG. 21 is a view for describing an outline of the twelfth example according to the present embodiment. For example, an information processing device 20 according to the present example may estimate a depressed state of a user on the basis of brain wave information collected by an information processing terminal 10 that is a wristband-type wearable device, and set a mental state of the user as an item to be improved. Furthermore, here, the information processing device 20 may estimate spare time of the user on the basis of information acquired from a schedule application that is a controlled object, and may present that a new schedule S1 related to "watching a movie" is added on a user interface UI5.

According to the information processing device 20 of the present example, it becomes possible to contribute to improvement in a mental state of a user by recommending a schedule for improving a depressed state for the user who likes to fill a schedule. In such a manner, the information processing device 20 according to the present embodiment can contribute to health improvement of a user by performing operation control of a controlled object even in a case other than a case where an item to be improved is improved.

2. Hardware Configuration Example

Figure 22:
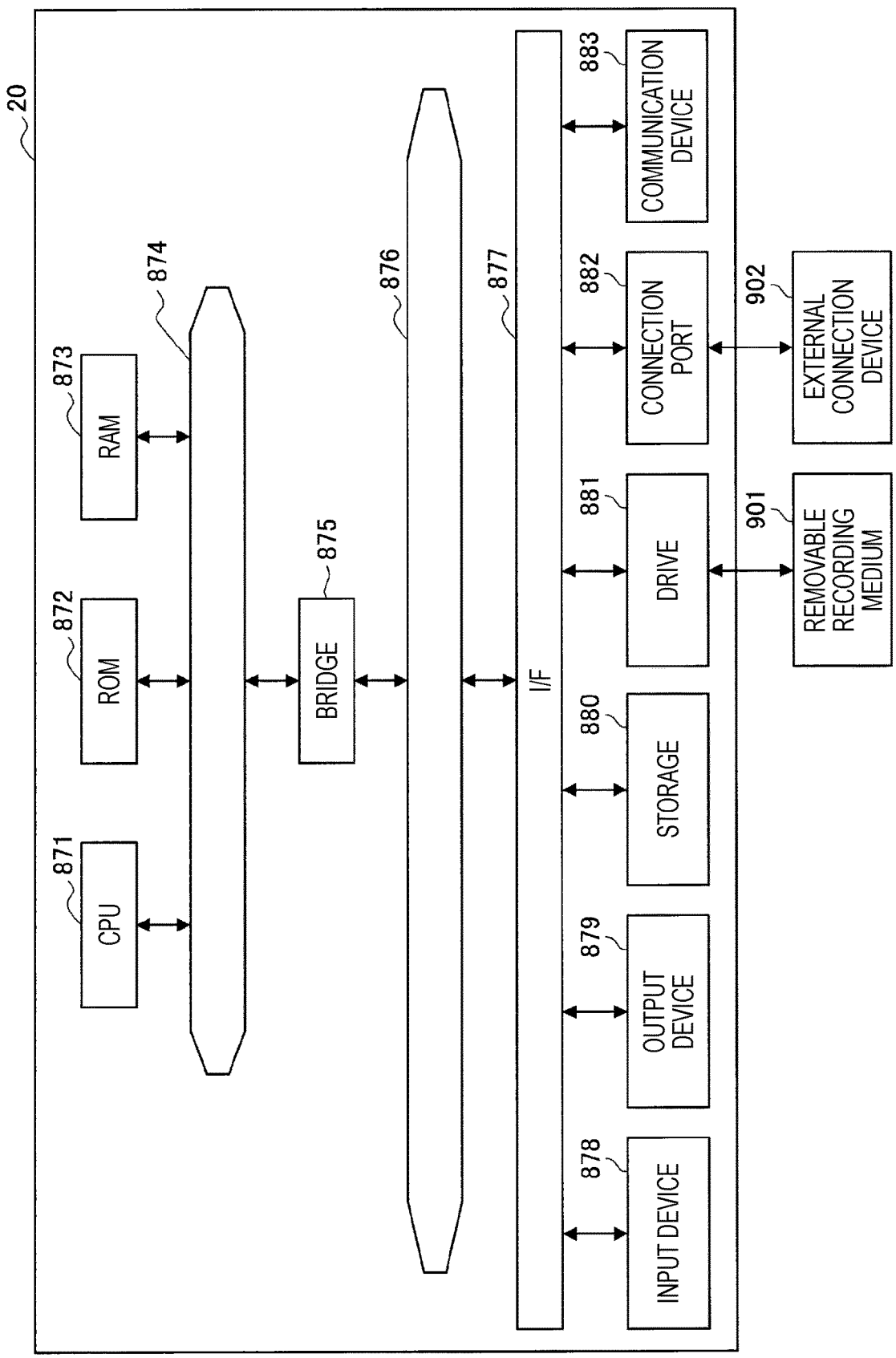
FIG. 22 is a view illustrating a hardware configuration example according to one embodiment of the present invention.

Next, a hardware configuration example that is common in an information processing terminal 10 and an information processing device 20 according to one embodiment of the present disclosure will be described. FIG. 22 is a block diagram illustrating a hardware configuration example of an information processing terminal 10 and an information processing device 20 according to one embodiment of the present disclosure. With reference to FIG. 22, each of the information processing terminal 10 and the information processing device 20 according to the present disclosure includes, for example, a CPU 871, a ROM 872, a RAM 873, a host bus 874, a bridge 875, an external bus 876, an interface 877, an input device 878, an output device 879, a storage 880, a drive 881, a connection port 882, and a communication device 883. Note that the hardware configuration described here is an example and a part of configuration elements may be omitted. Furthermore, a configuration element other than the configuration elements described here may be further included.

(CPU 871)

The CPU 871 functions, for example, as an arithmetic processing unit or a control device and controls a whole or part of an operation of each configuration element on the basis of various programs recorded in the ROM 872, the RAM 873, the storage 880, or a removable recording medium 901.

(ROM 872 and RAM 873)

The ROM 872 is a means that stores a program read by the CPU 871, data used for calculation, or the like. For example, the program read by the CPU 871, various parameters changed arbitrarily in execution of the program, or the like is temporarily or permanently stored in the RAM 873.

(Host Bus 874, Bridge 875, External Bus 876, and Interface 877)

The CPU 871, the ROM 872, and the RAM 873 are connected to each other, for example, through the host bus 874 that can perform high-speed data transmission. On the one hand, the host bus 874 is connected to the external bus 876 having a relatively low data transmission speed through the bridge 875, for example. Furthermore, the external bus 876 is connected to various configuration elements through the interface 877.

(Input Device 878)

For example, a mouse, a keyboard, a touch panel, a button, a switch, a lever, and the like are used as the input device 878. Moreover, there is a case where a remote controller (hereinafter, referred to as remote) that can transmit a control signal by using an infrared ray or a different radio wave is used as the input device 878. Furthermore, the input device 878 includes a sound input device such as a microphone.

(Output Device 879)

The output device 879 is a device that can visually or aurally notify a user of acquired information and that is, for example, a cathode ray tube (CRT), an LCD, a display device such as an organic EL, an audio output device such as a speaker or a headphone, a printer, a cell-phone, or a facsimile.

(Storage 880)

The storage 880 is a device to store various kinds of data. For example, a magnetic storage device such as a hard disk drive (HDD), a semiconductor storage device, an optical storage device, a magnetooptical storage device, or the like is used as the storage 880.

(Drive 881)

The drive 881 is, for example, a device that reads information recorded in the removable recording medium 901 such as a magnetic disk, an optical disk, a magnetooptical disk, or a semiconductor memory or writes information into the removable recording medium 901.

(Removable Recording Medium 901)

The removable recording medium 901 is, for example, a DVD medium, a Blu-ray (registered trademark) medium, an HD DVD medium, various semiconductor storage media, or the like. Obviously, the removable recording medium 901 may be an IC card in which a non-contact IC chip is mounted, an electronic device, or the like, for example.

(Connection Port 882)

For example, the connection port 882 is a port that is to connect an external connection device 902 and that is, for example, a universal serial bus (USB) port, an IEEE 1394 port, a small computer system interface (SCSI), an RS-232C port, or an optical audio terminal.

(External Connection Device 902)

The external connection device 902 is, for example, a printer, a portable music player, a digital camera, a digital video camera, an IC recorder, or the like.

(Communication Device 883)

The communication device 883 is a communication device for connection to a network and is, for example, a communication card for a wired or wireless LAN, Bluetooth (registered trademark), or a wireless USB (WUSB), a router for optical communication, a router for an asymmetric digital subscriber line (ADSL), various communication modems, or the like.

3. Conclusion

As described above, an information processing device 20 according to one embodiment of the present disclosure can calculate a health index of a user on the basis of collected sensor information. Furthermore, the information processing device 20 can set an item to be improved on the basis of the calculated health index, and determine an improving means to improve the item to be improved and a reward provided in a case where the item to be improved is improved. Furthermore, the information processing device 20 can present contents of the above improving means and reward to the user and can make a controlled object provide the reward in a case of determining that the item to be improved is improved. According to such a configuration, it becomes possible to more effectively encourage a user to make an action change related to improvement in a health condition.

In the above, a preferred embodiment of the present disclosure has been described in detail with reference to the attached drawings. However, the technical scope of the present disclosure is not limited to the above example. It is obvious that those skilled in the technical field of the present disclosure can come to find various modification examples or correction examples within the scope of the technical idea described in claims, and it is understood that these also belong to the technical scope of the present disclosure obviously.

Furthermore, an effect described in the present description is just explanation or exemplification and is not a limitation. That is, in addition to the above effect or instead of the above effect, a technology according to the present disclosure may have a different effect that is obvious to those skilled in the art from description in the present description.

Furthermore, each step related to processing by an information processing device 20 in the present description is not necessarily processed in time series in order described in a flowchart. For example, each step related to the processing by the information processing device 20 may be processed in order different from the order described in the flowchart or may be processed in parallel.

Note that configurations in the following manner also belong to a technical scope of the present disclosure.

(1)

An information processing device including:
a control unit configured to determine, on the basis of an item to be improved which item is set on the basis of a health index calculated from collected sensor information, an improving means to improve the item to be improved and a reward that is related to an amusement and that is served in a case where the item to be improved is improved, and configured to present contents of the improving means and the reward to a user,
in which the control unit determines whether or not the item to be improved is improved on the basis of a variation in the health index, and makes a controlled object perform an operation corresponding to the reward on the basis of the determination that the item to be improved is improved.

(2)

The information processing device according to (1),
in which the amusement includes a game, and
the controlled object includes a game application.

(3)

The information processing device according to (2),
in which the reward includes a bonus related to enhancement of a training object in the game application.

(4)

The information processing device according to (2) or (3),
in which the control unit determines the reward on the basis further of the health index of a different user.

(5)

The information processing device according to (1),
in which the control unit calculates a degree of influence of an action of the user, the action being estimated from the sensor information, on the health index and determines the improving means on the basis of the degree of influence.

(6)

The information processing device according to (5),
in which the improving means includes an action type and intensity of the action type, and
the control unit determines at least one of the action type or the intensity on the basis of the degree of influence.

(7)

The information processing device according to (6),
in which the control unit changes at least one of the improving means or the reward on the basis of non-performance, by the user, of an action corresponding to the action type.

(8)

The information processing device according to any one of (1) to (7),
in which the control unit determines at least one of the improving means or the reward on the basis further of an estimated condition of the user.

(9)

The information processing device according to (8),
in which the condition of the user includes at least one of a schedule or a physical condition of the user.

(10)

The information processing device according to any one of (1) to (9),
in which the control unit selects the controlled object corresponding to the determined reward.

(11)

The information processing device according to any one of (1) to (10), further including
a health index calculation unit that calculates the health index on the basis of the sensor information.

(12)

The information processing device according to (11),
in which the health index includes a plurality of different items, and
the health index calculation unit sets the item to be improved on the basis of a value of each of the plurality of different items.

(13)

The information processing device according to (11) or (12), in which the health index calculation unit sets the item to be improved on the basis further of the health index of a different user.

(14)

The information processing device according to any one of (1) to (13), further including
an action estimation unit that estimates an action of the user on the basis of the sensor information.

(15)

The information processing device according to (14),
in which the action estimation unit makes the estimated action of the user and the health index stored in association.

(16)

The information processing device according to any one of (1) to (15), further including
a condition estimation unit that estimates a condition of the user.

(17)

The information processing device according to any one of (1) to (16), further including
a presentation unit that presents contents of the improving means and the reward to the user on the basis of control by the control unit.

(18)

The information processing device according to any one of (1) to (17), further including
an operation unit that performs an operation corresponding to the reward on the basis of control by the control unit.

(19)

An information processing method including:
calculating, by a processor, a health index on the basis of collected sensor information;
setting an item to be improved on the basis of the health index;

determining an improving means to improve the item to be improved and a reward that is related to an amusement and that is served in a case where the item to be improved is improved;

presenting contents of the improving means and the reward to a user;

determining whether or not the item to be improved is improved on the basis of a variation in the health index; and performing an operation corresponding to the reward on the basis of the determination that the item to be improved is improved.

(20)

A program for causing a computer to function as an information processing device including a control unit configured to determine, on the basis of an item to be improved which item is set on the basis of a health index calculated from collected sensor information, an improving means to improve the item to be improved and a reward that is related to an amusement and that is served in a case where the item to be improved is improved, and configured to present contents of the improving means and the reward to the user, in which the control unit determines whether or not the item to be improved is improved on the basis of a variation in the health index, and makes a controlled object perform an operation corresponding to the reward on the basis of the determination that the item to be improved is improved.

REFERENCE SIGNS LIST

10 Information processing terminal
110 Sensor unit
120 Input unit
130 Output unit
140 Terminal control unit
150 Communication unit
20 Information processing device
210 Health index calculation unit
220 Sensor DB
230 Action estimation unit
240 Action-index DB
250 Condition estimation unit
260 Control unit
270 Presentation unit
280 Operation unit
30 Controlled object

The invention claimed is:

1. An information processing device, comprising:
a processor configured to:
  acquire sensor information;
  set an item based on a health index of a first user, wherein the health index is based on the sensor information;
  determine, based on the item, a reward and an improving process to improve the item, wherein the reward is related to an amusement;
  control presentation of contents of the improving process and the reward to the first user;
  determine the improvement of the item based on a variation in the health index, wherein a provision of the reward is based on the improvement of the item; and
  control, based on the determination of the improvement of the item, a controlled object to execute an operation corresponding to the reward.

2. The information processing device according to claim 1, wherein
the amusement includes a game, and
the controlled object includes a game application.

3. The information processing device according to claim 2, wherein
the reward includes a bonus related to enhancement of a training object in the game application.

4. The information processing device according to claim 2, wherein
the processor is further configured to determine the reward based on a health index of a second user, and
the second user is different from the first user.

5. The information processing device according to claim 1, wherein the processor is further configured to:
  estimate an action of the first user based on the sensor information;
  calculate a degree of influence of the action of the first user on the health index; and
  determine the improving process based on the degree of influence.

6. The information processing device according to claim 5, wherein
the improving process includes an action type and intensity of the action type, and
the processor is further configured to determine at least one of the action type or the intensity based on the degree of influence.

7. The information processing device according to claim 6, wherein
the processor is further configured to change at least one of the improving process or the reward based on non-performance, of the action corresponding to the action type.

8. The information processing device according to claim 1, wherein
the processor is further configured to determine at least one of the improving process or the reward based on a condition associated with the first user.

9. The information processing device according to claim 8, wherein
the condition associated with the first user includes at least one of a schedule or a physical condition of the first user.

10. The information processing device according to claim 1, wherein
the processor is further configured to select the controlled object corresponding to the determined reward.

11. The information processing device according to claim 1, wherein the processor is further configured to calculate the health index of the first user based on the sensor information.

12. The information processing device according to claim 11, wherein
the health index includes a plurality of different items, and
the processor is further configured to set the item based on a value of each of the plurality of different items.

13. The information processing device according to claim 11, wherein
the processor is further configured to set the item based on a health index of a second user, and
the second user is different from the first user.

14. The information processing device according to claim 1, wherein the processor is further configured to estimate an action of the first user based on the sensor information.

15. The information processing device according to claim 14, wherein the processor is further configured to control storage of the estimated action of the first user in association with the health index of the first user.

16. The information processing device according to claim 1, wherein the processor is further configured to estimate a condition of the first user.

17. The information processing device according to claim 1, further comprising a display screen configured to present the contents of the improving process and the reward to the first user based on the control by the processor.

18. The information processing device according to claim 1, wherein the controlled object includes a game application.

19. An information processing method, comprising:
    acquiring, by a processor of an information processing device, sensor information;
    calculating, by the processor, a health index of a user based on the sensor information;
    setting, by the processor, an item based on the health index of the user;
    determining, by the processor, an improving process and a reward based on the item, wherein
        the improving process improves the item, and
        the reward is related to an amusement;
    controlling, by the processor, presentation of contents of the improving process and the reward to the user;
    determining, by the processor, the improvement of the item based on a variation in the health index, wherein a provision of the reward is based on the improvement of the item; and
    controlling, by the processor, a controlled object to execute an operation corresponding to the reward, wherein the controlled object is controlled based on the determination of the improvement of the item.

20. A non-transitory computer-readable medium having stored thereon computer-executable instructions which, when executed by a processor of an information processing device, cause the processor to execute operations, the operations comprising:
    acquiring sensor information;
    calculating a health index of a user based on the sensor information;
    setting an item based on the health index of the user;
    determining an improving process and a reward based on the item, wherein
        the improving process improves the item, and
        the reward is related to an amusement;
    controlling presentation of contents of the improving process and the reward to the user;
    determining the improvement of the item based on a variation in the health index, wherein a provision of the reward is based on the improvement of the item; and
    controlling, based on the determination of the improvement of the item, a controlled object to execute an operation corresponding to the reward.

* * * * *